US007611452B2

(12) United States Patent
Allison et al.

(10) Patent No.: US 7,611,452 B2
(45) Date of Patent: Nov. 3, 2009

(54) WIZARD AND TEMPLATE FOR TREATMENT PLANNING

(75) Inventors: John W. Allison, Los Altos, CA (US);
John R. Dooley, Castro Valley, CA (US);
Jay B. West, Mountain View, CA (US);
Gopinath Kuduvalli, San Jose, CA (US);
Hongwu Wang, Milpitas, CA (US);
Jin-Wu J. Wang, Palo Alto, CA (US);
Warren Kilby, Swinford (GB);
Derek Olender, San Jose, CA (US);
Michael Saracen, Oakland, CA (US)

(73) Assignee: Accuray Incorporated, Sunnyvale, CA (US)

(*) Notice: Subject to any disclaimer, the term of this patent is extended or adjusted under 35 U.S.C. 154(b) by 506 days.

(21) Appl. No.: 11/242,219

(22) Filed: Sep. 30, 2005

(65) Prior Publication Data

US 2007/0078306 A1 Apr. 5, 2007

(51) Int. Cl.
*A61N 5/00* (2006.01)
(52) U.S. Cl. .......................................................... 600/1
(58) Field of Classification Search ................ 600/1–8, 600/300, 424; 128/897, 898, 920–924; 378/64, 378/65; 604/20
See application file for complete search history.

(56) References Cited

U.S. PATENT DOCUMENTS

| 6,385,286 | B1* | 5/2002 | Fitchard et al. ............... 378/65 |
| 7,066,883 | B2* | 6/2006 | Schmidt et al. ............. 600/300 |
| 7,362,848 | B2* | 4/2008 | Saracen et al. ................ 378/65 |
| 2003/0208108 | A1* | 11/2003 | Shewmake et al. .......... 600/300 |

OTHER PUBLICATIONS

PCT International Search Report and Written Opinion of the International Searching Authority, PCT/US06/36874 filed Sep. 19, 2006, 8 pages.

* cited by examiner

*Primary Examiner*—Samuel G Gilbert
(74) *Attorney, Agent, or Firm*—Blakely, Sokoloff, Taylor & Zafman LLP

(57) ABSTRACT

An interface is provided to a user to perform a plurality of treatment planning operations associated with the treatment plan before the treatment plan is optimized. The treatment planning operations include at least one of selecting a treatment planning parameter or inputting data corresponding to the treatment planning parameter. One or more templates containing one or more pre-defined treatment planning parameters are provided to the user to enable the user to skip performing one or more of the plurality of operations.

22 Claims, 18 Drawing Sheets
(14 of 18 Drawing Sheet(s) Filed in Color)

WIZARD AND TEMPLATE FOR TREATMENT PLANNING

TECHNICAL FIELD

The present invention relates generally to radiation treatment and, more particularly, to treatment planning.

BACKGROUND

Tumors and lesions are types of pathological anatomies characterized by abnormal growth of tissue resulting from the uncontrolled, progressive multiplication of cells, while serving no physiological function.

Pathological anatomies can be treated with an invasive procedure, such as surgery, but can be harmful and full of risks for the patient. A non-invasive method to treat a pathological anatomy (e.g., tumor, legion, vascular malformation, nerve disorder, etc.) is external beam radiation therapy. In one type of external beam radiation therapy, an external radiation source is used to direct a sequence of x-ray beams at a tumor site from multiple angles, with the patient positioned so the tumor is at the center of rotation (isocenter) of the beam. As the angle of the radiation source changes, every beam passes through the tumor site, but passes through a different area of healthy tissue on its way to the tumor. As a result, the cumulative radiation dose at the tumor is high and the average radiation dose to healthy tissue is low.

The term "radiotherapy" refers to a procedure in which radiation is applied to a target region for therapeutic, rather than necrotic, purposes. The amount of radiation utilized in radiotherapy treatment sessions is typically about an order of magnitude smaller, as compared to the amount used in a radiosurgery session. Radiotherapy is typically characterized by a low dose per treatment (e.g., 100-200 centiGray (cGy)), short treatment times (e.g., 10 to 30 minutes per treatment) and hyperfractionation (e.g., 30 to 45 days of treatment). For convenience, the term "radiation treatment" is used herein to mean radiosurgery and/or radiotherapy unless otherwise noted by the magnitude of the radiation.

Conventional isocentric radiosurgery systems (e.g., the Gamma Knife) use forward treatment planning. In forward treatment planning, a medical physicist determines the radiation dose to be applied to a tumor and then calculates how much radiation will be absorbed by critical structures (i.e., vital organs) and other healthy tissue. There is no independent control of the two dose levels for a given number of beams, because the volumetric energy density at any given distance from the isocenter is a constant, no matter where the isocenter is located.

In inverse planning, in contrast to forward planning, the medical physicist specifies the minimum dose to the tumor and the maximum dose to other healthy tissues independently, and the treatment planning software then selects the direction, distance, and total number and energy of the beams in order to achieve the specified dose conditions. Conventional treatment planning software packages are designed to import 3-D images from a diagnostic imaging source, for example, computerized x-ray tomography (CT) scans. CT is able to provide an accurate three-dimensional model of a volume of interest (e.g., skull or other tumor bearing portion of the body) generated from a collection of CT slices and, thereby, the volume requiring treatment can be visualized in three dimensions.

During inverse planning, a volume of interest (VOI) is used to delineate structures to be targeted or avoided with respect to the administered radiation dose. That is, the radiation source is positioned in a sequence calculated to localize the radiation dose into a VOI that as closely as possible conforms to the tumor requiring treatment, while avoiding exposure of nearby healthy tissue. Once the target (e.g., tumor) VOI has been defined, and the critical and soft tissue volumes have been specified, the responsible radiation oncologist or medical physicist specifies the minimum radiation dose to the target VOI and the maximum dose to normal and critical healthy tissue. The software then produces the inverse treatment plan, relying on the positional capabilities of the radiation treatment system, to meet the min/max dose constraints of the treatment plan.

FIG. 1 is a conceptual illustration of a graphical output of a treatment planning software displaying a slice of a CT image. The illustration of the CT image includes a pathological anatomy that is targeted for treatment, and well as a critical region that is positioned near the pathological anatomy. The treatment planning software enables the generation of a critical region contour around the critical region and a target region contour around the pathological anatomy. Conventionally, a user manually delineates points (e.g., some of the dots on the contour lines of FIG. 1) on the display that is used by the treatment planning software to generate the corresponding contours. While this may seem an easy task, such matching is difficult due to the three-dimensional nature and irregularities of the pathological and normal anatomies, and the limited number of beam positions available from the radiation beam source. Based on specified minimum dose to the target region and the maximum dose to the critical region, the treatment planning software generates a dose isocontour for the target region. The dose isocontour represents a given dose percentage (e.g., 60%, 70%, 80%, etc.) of a specified prescription dose for the target region. Ideally, the dose isocontour should perfectly match the contour of the target region. In some cases, the dose isocontour generated by the treatment planning software is not optimal, and can include portions of the critical region, as illustrated in FIG. 1.

The two principal requirements for an effective radiation treatment system are homogeneity and conformality. Homogeneity is the uniformity of the radiation dose over the volume of the target (e.g., pathological anatomy such as a tumor, lesion, vascular malformation, etc.) characterized by a dose volume histogram (DVH). An ideal DVH for the pathological anatomy would be a rectangular function as illustrated in FIG. 2, where the dose is 100 percent of the prescribed dose over the volume of the pathological anatomy and zero elsewhere. A desirable DVH for a critical region would have the profile illustrated in FIG. 3, where the volume of the critical anatomical structures receives as little of the prescribed dose as possible.

Conformality is the degree to which the radiation dose matches (conforms) to the shape and extent of the target (e.g., tumor) in order to avoid damage to critical adjacent structures. More specifically, conformality is a measure of the amount of prescription (Rx) dose (amount of dose applied) within a target VOI. Conformality may be measured using a conformality index (CI)=total volume at>=Rx dose/target volume at>=Rx dose. Perfect conformality results in a CI=1. With conventional radiotherapy treatment, using treatment planning software, a clinician identifies a dose isocontour for a corresponding VOI for application of a treatment dose (e.g., 3000 cGy).

The treatment planning process typically requires a user to employ a treatment planning software program to complete several planning functions. The user interface of the treatment planning software guides the user to complete the treatment plan. For example, the first step in treatment planning may be selecting and loading patient data into the treatment planning software program. This function allows the user to load previously saved plans, start a new plan by loading DICOM formatted patient data, including volumes of interest pushed as DICOM RT structure sets, recover the last plan worked on, or delete a previously saved plan. For example, the load function may involve three tasks that are performed within a single user-interface window, as shown in FIG. 4. The first task may be to select a fixed image (e.g., CT image) for the patient by selecting the patient, study, and series. A similar process may be performed for selecting a moving image (e.g., MR, PET). One problem associated with the load function is that because multiple tasks are performed within a single user-interface window, the load function may be confusing or overly complicated for some users, particularly users that are new to the treatment planning software program.

The treatment planning software typically allows the user to set display preferences and defaults for such settings as Isocurve parameters, VOI Set parameters, and density model for dose calculations. Because treatment plans differ from patient to patient, as well as from treatment region to treatment region (e.g., cranial versus lung), the treatment planning software requires the user to input parameters throughout the treatment planning process. One problem with such a process is that the chances of user based errors are increased because of the number of manual inputs. Moreover, such manual tasks are time consuming and may unnecessarily increase the overall time spent on treatment planning.

The treatment planning software may also provide the option to set preferences through a preference screen, for example, as shown in FIG. 5. One problem with such preference screens is that they may be limited to basic settings and do not allow the user to set parameters related to a treatment plan. For example, the preference screen may be limited to colors for isocurve lines and colors for various VOI names.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention is illustrated by way of example, and not by way of limitation, in the figures of the accompanying drawings.

DETAILED DESCRIPTION

Figure 1:
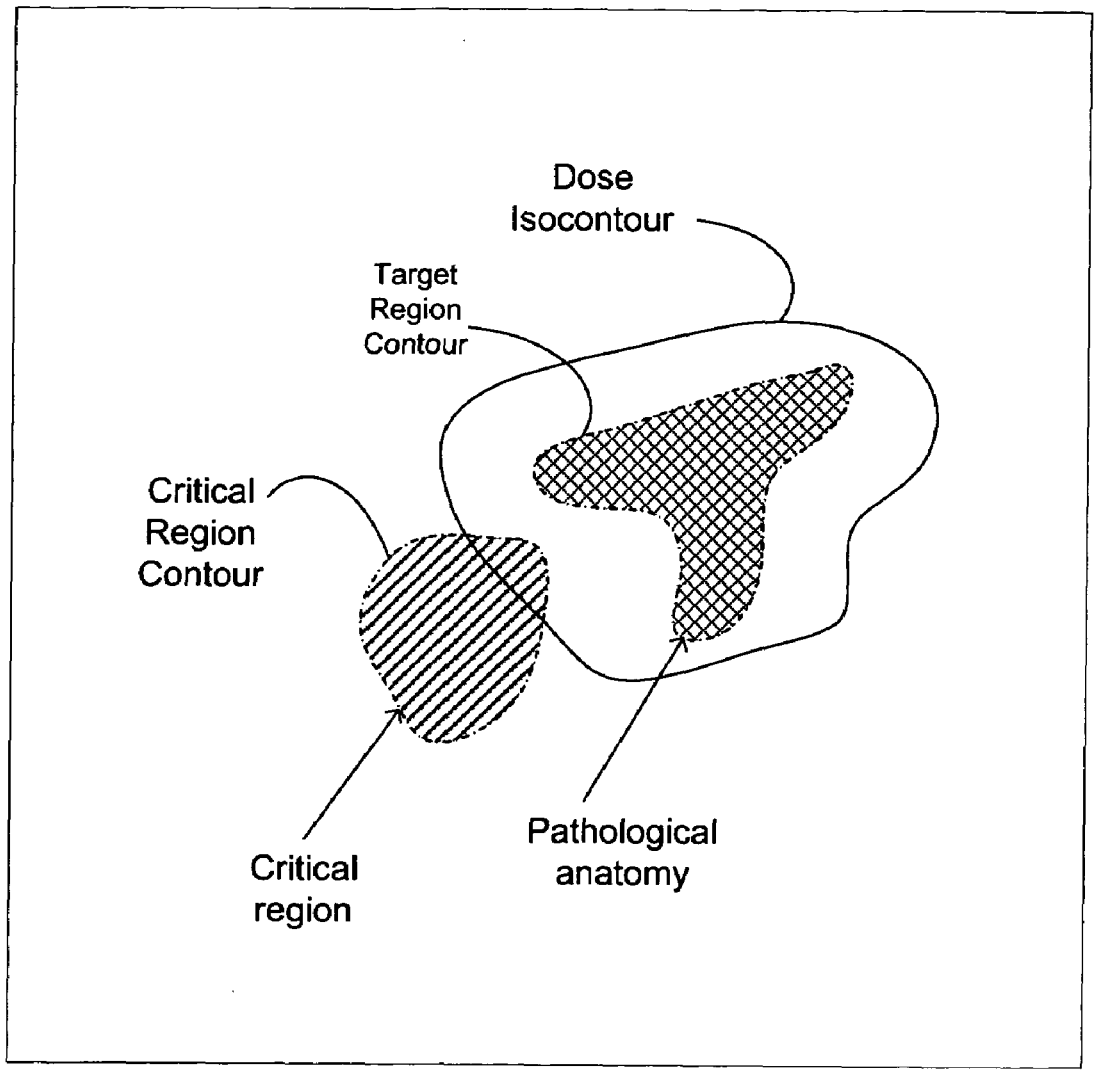
FIG. 1 illustrates a graphical output of a treatment planning software displaying a slice of a CT image.
Figure 2:
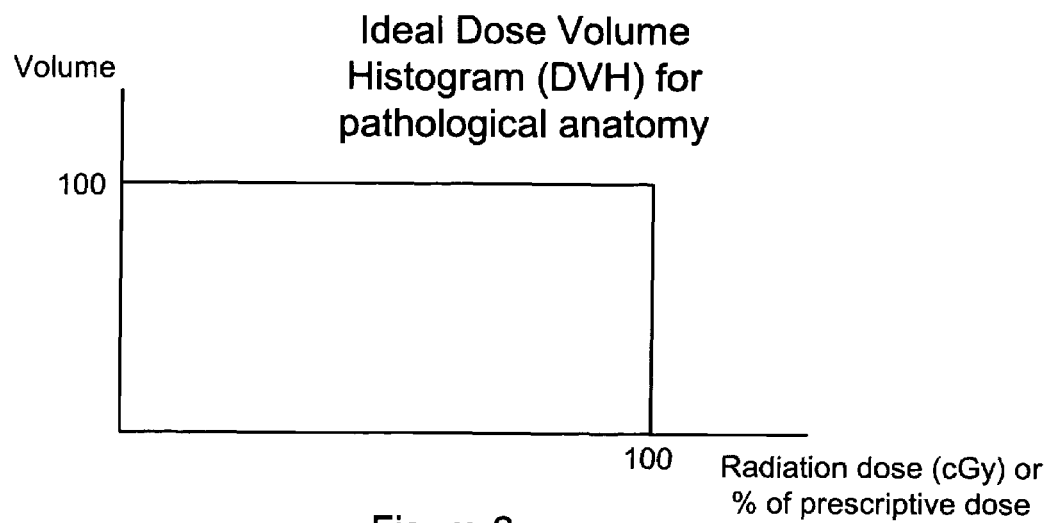
FIG. 2 is an ideal DVH for a pathological anatomy.
Figure 3:
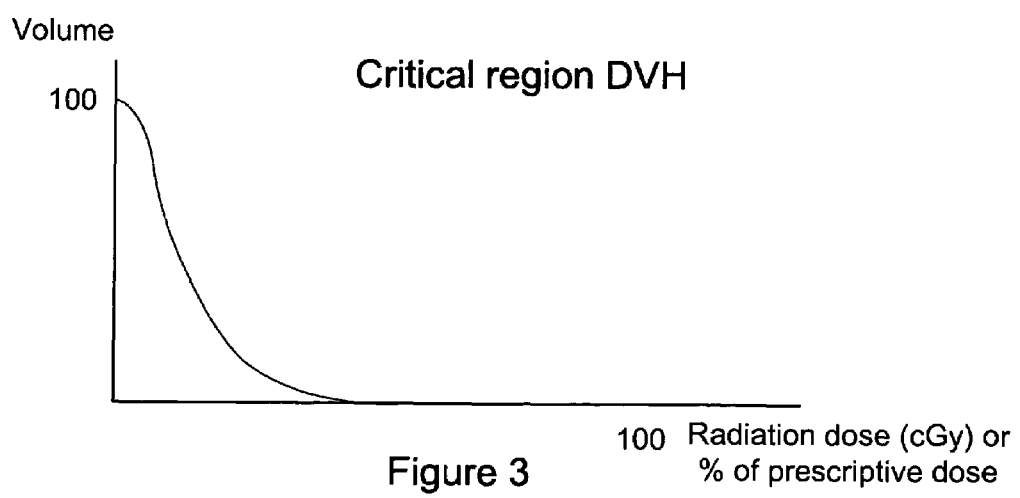
FIG. 3 is a desirable DVH for a critical region.

In the following description, numerous specific details are set forth such as examples of specific systems, components, methods, etc. in order to provide a thorough understanding of the present invention. It will be apparent, however, to one skilled in the art that these specific details need not be employed to practice the present invention. In other instances, well-known components or methods have not been described in detail in order to avoid unnecessarily obscuring the present invention.

Embodiments of the present invention include various steps, which will be described below. The steps of the present invention may be performed by hardware components or may be embodied in machine-executable instructions, which may be used to cause a general-purpose or special-purpose processor programmed with the instructions to perform the steps. Alternatively, the steps may be performed by a combination of hardware and software.

Embodiments of the present invention may be provided as a computer program product, or software, that may include a machine-readable medium having stored thereon instructions, which may be used to program a computer system (or other electronic devices) to perform a process. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; electrical, optical, acoustical, or other form of propagated signal (e.g., carrier waves, infrared signals, digital signals, etc.); or other type of medium suitable for storing electronic instructions.

Embodiments of the present invention may also be practiced in distributed computing environments where the machine-readable medium is stored on and/or executed by more than one computer system. In addition, the information transferred between computer systems may either be pulled or pushed across the communication medium connecting the computer systems, such as in a remote diagnosis or monitoring system. In remote diagnosis or monitoring, a user may utilize embodiments of the present invention to diagnose or monitor a patient despite the existence of a physical separation between the user and the patient. In addition, the treatment delivery system may be remote from the treatment planning system.

A method of treatment planning and a treatment planning system are described, which include a treatment planning software (referred to as "TPS" herein). In one embodiment, one or more portions of the TPS involves a "wizard" or "wizard-like" user interface, in which the TPS guides the user through one or complex tasks of treatment planning. For example, the TPS wizard may involve step-by-step dialogs to guide the user through the treatment planning process. In one embodiment, the wizard user interface may be used to focus the treatment planning process to a particular treatment region of the patient.

In an alternative embodiment, the TPS may allow the user to incorporate one or more templates into treatment planning process. These templates may provide one or more pre-defined treatment planning parameters and settings applicable to the anatomical treatment region of interest. For example, during treatment planning, the user may specify an anatomical region targeted for radiation treatment. A body graphic indicating treatment sites or applications can be used as part of the user interface. Based on the selected body region, a library of suitable planning templates is uploaded with pre-defined planning parameters. The parameter settings for the templates may be based on past treatments that were successful for a particular body region (e.g., cranial, spine, lung). In one embodiment, parameter settings may be pre-defined by the factory (e.g., the manufacturer of the TPS), pre-defined and saved by the user, or pre-defined from a learning processes by the system from previous plans for the same treatment site. One such parameter setting may be a node set (or subset) best suited for optimizing treatment plan conformality, DVH, and delivery times. The user can review, modify, and accept template planning parameter values before beginning the plan. The user may also modify template parameters and save under a new template name. The use of a wizard user interface and templates, either alone or in combination, provides the advantage of reducing the time required to complete the treatment planning process, reducing user error, and may also provide a method to simplify the various task involved in the treatment planning workflow.

In one embodiment, the TPS is implemented on the Windows XP® product platform (alternatively, other operating system platforms may be used), and is designed to integrate with the CyberKnife® System and third-party imaging systems seamlessly. In one embodiment, the TPS is fully compliant with the DICOM-RT standard for the distribution and viewing of medical images, and the TPS is pre-configured with these utilities and requires no additional software.

In one embodiment, the TPS provides a wizard or wizard-like user interface to launch the treatment planning process. The wizard guides the user into the workflow for treatment planning. The workflow for treatment planning may be organized into six planning tasks.

(1) LOAD. The user selects and loads patient data with the use of an interactive wizard, including the option to select templates for use during the treatment planning process. The templates may include parameter settings such as treatment anatomy, template path set, and pre-defined VOIs.

(2) FUSE. If the user chooses two or more medical images (e.g., different types of image modalities such as CT and PET images) to generate a treatment plan, this task allows the user to fuse the images so they are aligned to the same physical space.

(3) ALIGN. The user sets the treatment modes, identifies fiducials, and aligns the nominal patient position within the detectors of the imaging system.

(4) CONTOUR. The user contours anatomical volumes of interest.

(5) PLAN. The user can generate and modify isocentric and non-isocentric plans. The user can also evaluate the dose distribution for the plan.

(6) VISUALIZE. The user can view an array of the two-dimensional image slices or merge and filter volume renderings of the patient anatomy.

The TPS also includes three ancillary tasks that provide advanced plan evaluation tools, system quality assurance tools, preference settings, and on-line assistance.

(1) Plan Quality Assurance. The user can compare two potential plans for the same treatment. The user can also sum two or more plans for the same patient. The user can display the dose distribution for the plan as treated to a phantom during a film test. The user can animate robot delivery of the treatment plan.

(2) Settings. This task includes a tool to center the dose distribution for a ball-cube plan. The interface displays the list of beams and their geometric patterns for the current plan. The user can set color preference for the isodose curves, VOIs, and screen overlays. The user can also set the behavior of the zoom and pan controls.

(3) Help. The user manual for the TPS can be accessed online.

In one embodiment, the TPS provides a user with a multiple tier task/step/function workflow-based approach to treatment planning in which the user is forced to perform a certain enabled task (e.g., fuse), steps within the task (e.g., the seed points and register steps of the Fuse task), and functions within the step (start and pause function of Register step), by being provided a view that only enables the user to interface with the certain enabled task (e.g., a preceding task), before the user is given the ability to perform another task (e.g., a proceeding task) in the TPS by being provided another user interface view corresponding to the other task. Alternatively, the user may be allowed to perform one or more of the tasks, or steps within a task, out of sequence or before completing other tasks and/or steps. Details of exemplary tasks and their associated steps and functions are discussed below.

Figure 6:
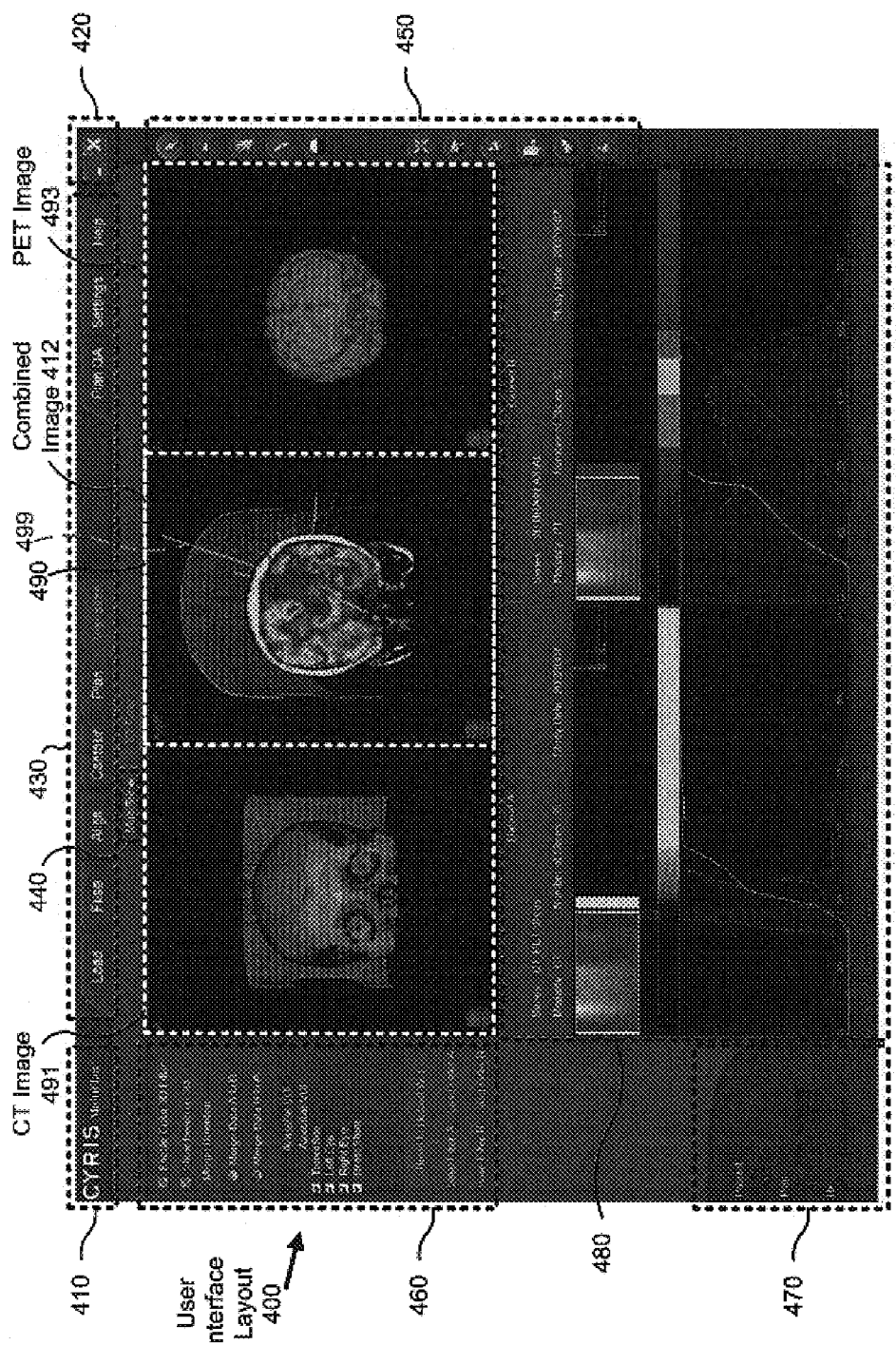
FIG. 6 illustrates one example of a user interface layout for a treatment planning software program.

FIG. 6 illustrates one example of a TPS user interface layout 400. In one embodiment, the screen layout of the user interface is divided into, for example, seven areas. In this exemplary embodiment, the seven areas on the screen layout include:

(1) Identification. The top left area 410 identifies the TPS as part of a particular product line (e.g., CYRIS™ product line). The top right area 420 includes minimize and exit controls.

(2) Task/Step Control. In one embodiment, the top menu bar 430 lists the tasks (e.g., Load, Fuse, Align, Contour, Plan, and Visualize). Below the menu bar 430 is an area 440 with a list of the steps contained in a selected task.

(3) Global Controls. Along the right side of the display are the global controls 450 that permit the user to access functions that may be desired during any of the steps in the planning workflow.

(4) Control View. The middle left of the display includes the controls 460 available for the currently selected step (e.g. Visualize). Each step may have a different set of controls.

(5) Display View. The large display center area 490 includes the display of the medical images and other large graphical and text controls. In the exemplary illustrated embodiment of FIG. 6, the user interface layout 400 includes a CT image 491, a PET image 493, and a combined CT/PET image 492. The CT/PET image may be combined with a fusion process to display the images in a common space. In one embodiment, the combined CT/PET image may also include a display of the beam paths (e.g., beam path 499) that are generated according to the treatment plan.

A VOI inside an object volume is defined as a geometry object. In radiosurgery applications, for example, tumor and critical structures can be defined as volume of interest based on the patient image, such as CT or MRI. Volume rendering can render both volume and VOI info. There are different ways to render VOI information on top of volume information. In one embodiment, embedded geometry rendering may be used, which uses surface rendering technique to render the embedded geometry information into the volume rendering image. In an alternative embodiment, VOI information may be rendered on top of volume information by converting the VOI geometry to special volume information before the rendering. The VOI and volume information is rendered by using a volume rendering method at the same time.

In another embodiment, the combined image may also include a display of other treatment parameters, for example, a VOI structure and a dose contour. It should be noted that, alternatively, types of images of than CT and/or PET may be displayed (e.g., MRI, ultrasound, etc.) Each step may have a different display layout. For some steps, the user may be able to select the display layout.

(6) Patient Identification. The bottom left area 470 displays patient and plan information, including patient name and medical ID, plan name, date and time the plan was saved, and the prescription percentage and dose.

(7) Status. The bottom center and right areas 480 display status. The position of the image focus and value of the image gray scale number appear on the right. On the left is general information, including a time-elapsed bar.

In one embodiment, the Load task may be accomplished with the aid of a wizard to launch the workflow process for treatment planning. The wizard guides the user through one or more steps, and in one embodiment, four steps are involved to launch the treatment planning workflow. The four wizard steps include Select Patient, Select Primary Exam, Select Additional Exams, and Select Template.

Figure 7:
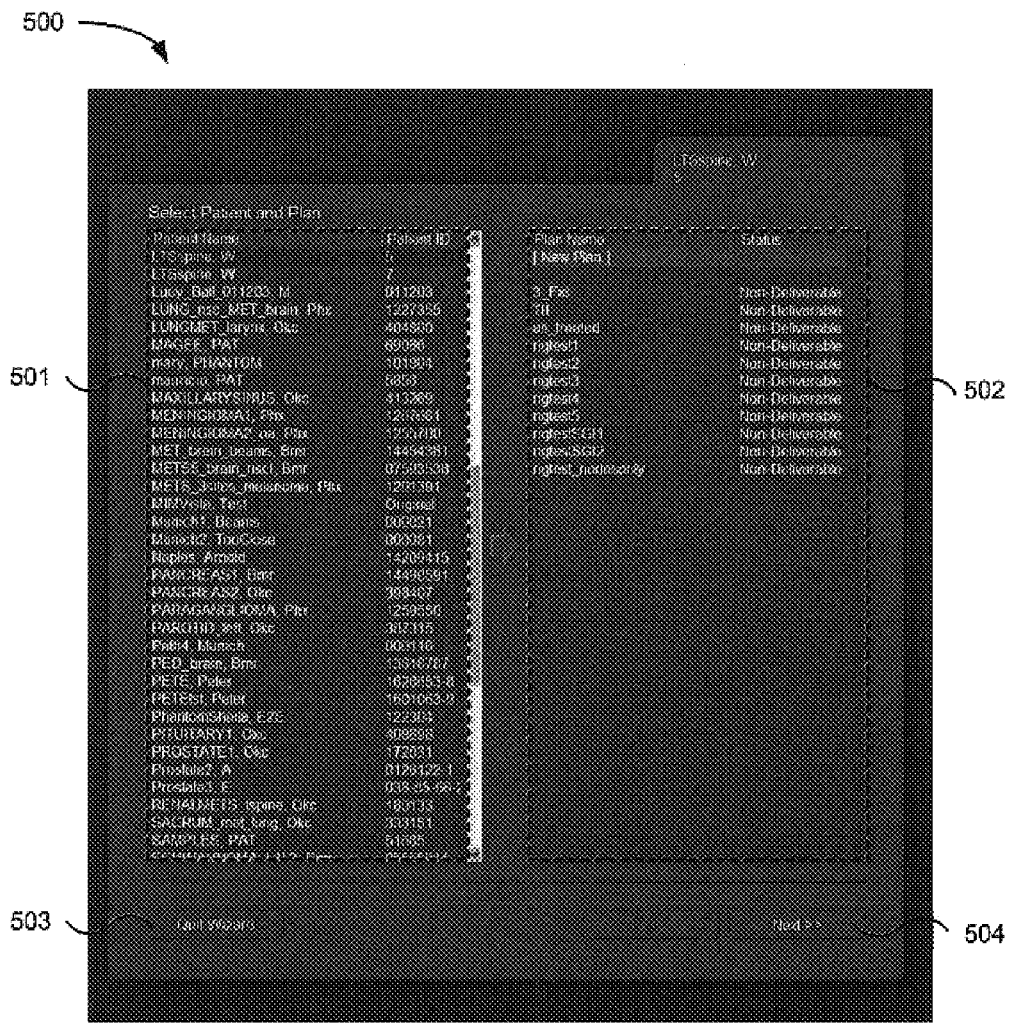
FIG. 7 illustrates an example of a user interface for the first wizard step.

FIG. 7 illustrates an example of a user interface 500 for the first wizard step, Select Patient. In this step, the user selects the patient, and a plan corresponding to the selected patient. The name and ID of the user selected patient is displayed on the title of the wizard frame window. The windows in the wizard view of FIG. 7 include patient list 501 and plan list 502. The patient list 501 displays the entire list of the available patients in a patient database. The plan list 502 contains all the plans that have been created under the current selected patient. Alternatively, a new plan may be created for the selected patient. This wizard window of interface 500 also provides the option of exiting the wizard framework (e.g., button 503), which in one embodiment, defaults the user to the load step of the standard workflow (e.g., the user interface of FIG. 4).

Figure 8:
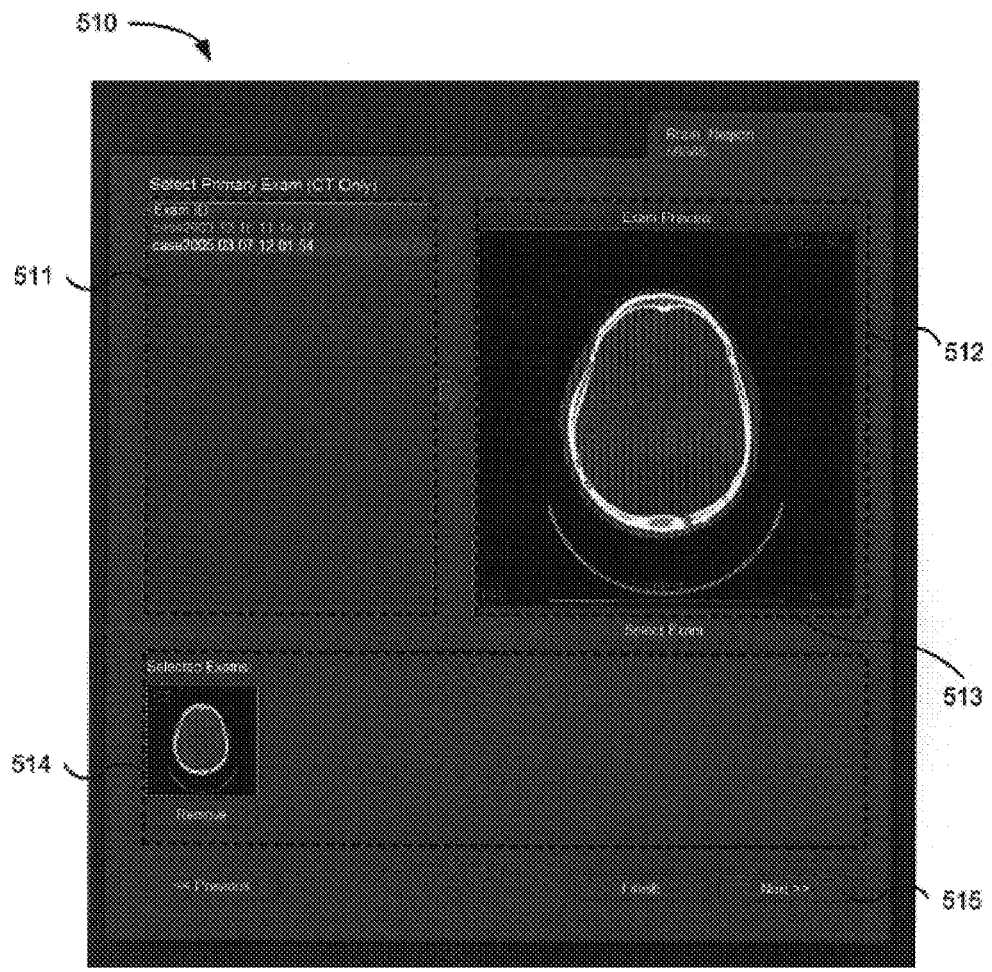
FIG. 8 illustrates an example of a user interface for the second wizard step.

By pressing the "Next" button 504, the TPS leads the user to the next wizard step, Select Primary Exam. This second wizard step is shown in the user interface 510 of FIG. 8. In this step, the user selects the primary image for treatment planning (e.g., a CT image). For example, the wizard interface of FIG. 8 shows a window 511 with the available CT images for the selected patient, and a preview window 512 to display the selected CT image. In one embodiment, the preview window automatically displays the middle slice of the selected CT image. A progress bar 513 for the sorting of the CT image slices is also provided in the wizard frame. The snapshot view 514 displays the current selected primary CT image, and when an image is selected in the snapshot view 514, that particular image flashes for a few seconds.

Figure 9:
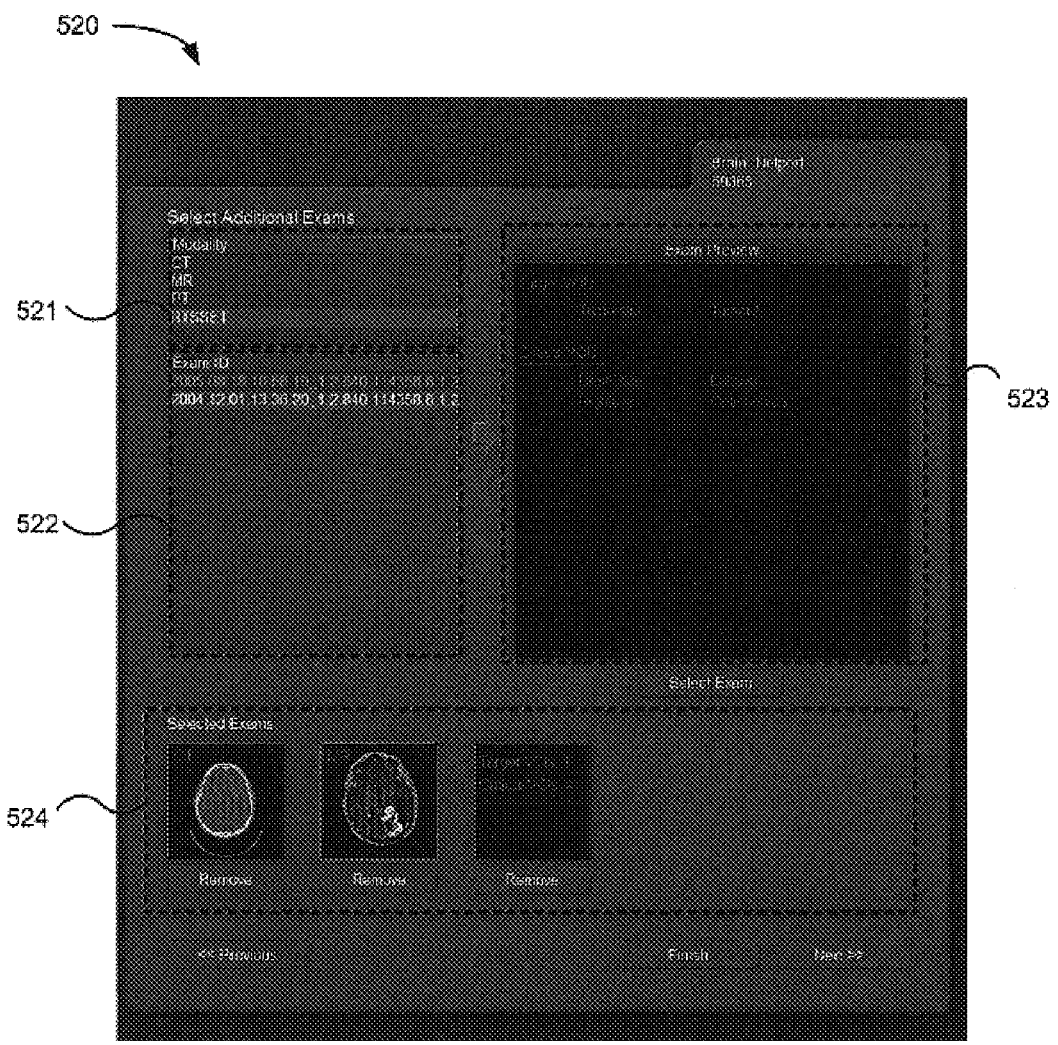
FIG. 9 illustrates an example of a user interface for the third wizard step.

After completing the Select Primary Exam step, the user may then press "Next" 515 for the next wizard step, Select Additional Exams. In this step, the user selects additional images from other types of image modalities and/or formats, such as MR, PET, and DICOM structure sets. This third wizard step is shown in the user interface 520 of FIG. 9. The user interface of this wizard frame may be substantially similar to the user interface of FIG. 8 (i.e., Select Primary Exam). A list of available image modalities is provided in modality window 521, and when a particular image modality is clicked, a list of available images is displayed in image window 522. The preview window 523 displays the selected image. The snapshot views 524 display the image from the Select Primary Exam step as well as the images from the Select Additional Exams step.

Figure 10:
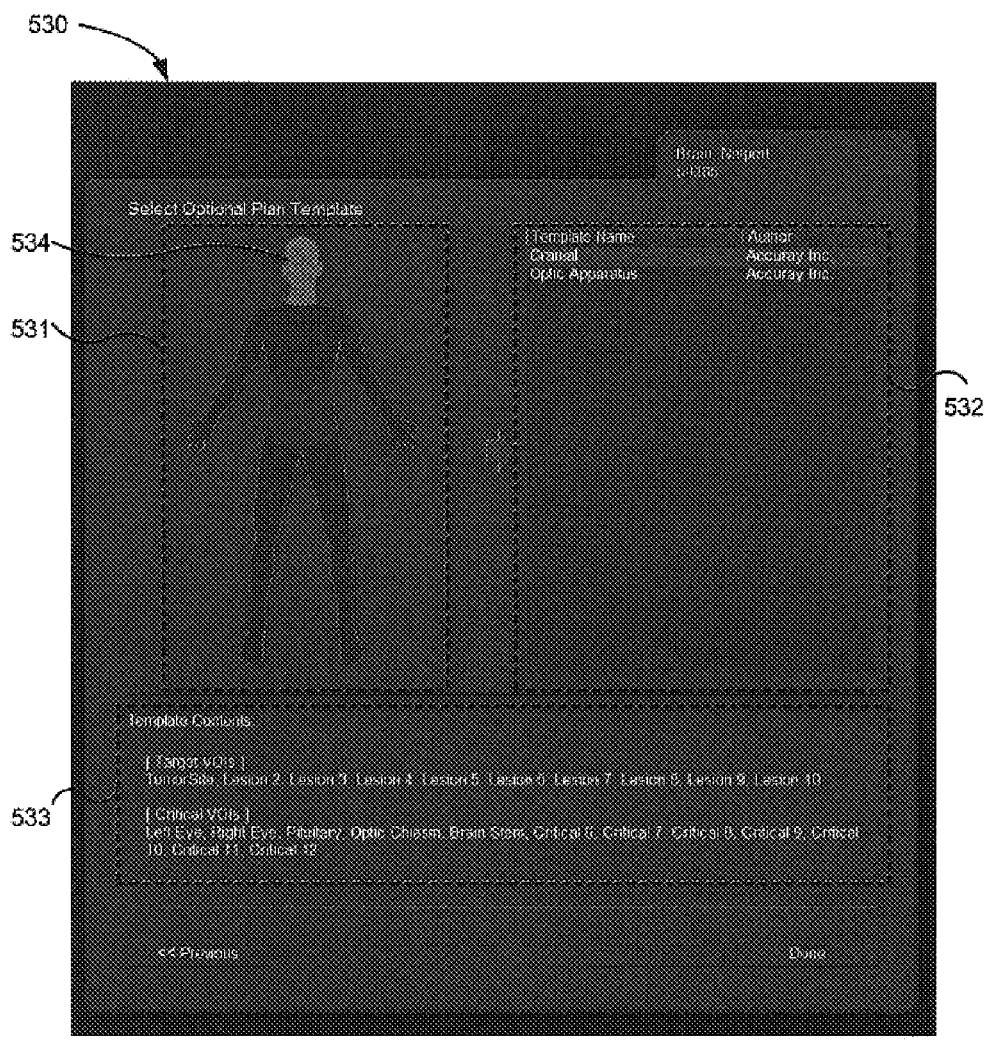
FIG. 10 illustrates an example of a user interface for the select template step of the wizard process.

The final step of the wizard user interface is Select Plan Template, shown in the user interface 530 of FIG. 10. The wizard view of this step may include three controls: the region selector 531, the template list 532, and the description window 533. The region selector 531 displays a full-body human model. When a user moves a mouse or cursor control over different parts of the human model, or alternatively clicks on one of the regions, the selector highlights that region with a different color (e.g., cranial region 534). In one embodiment, for example, the human model is divided into four regions: Head and Neck, Chest, Abdomen, and Others. The template list 532 displays all templates that belong to the current selected body region. Templates can be created, or modified through a template management user interface. The template description window 533 displays the detail of the current selected plan template. In one embodiment, the names of the VOIs in the template may be displayed.

Figure 11:
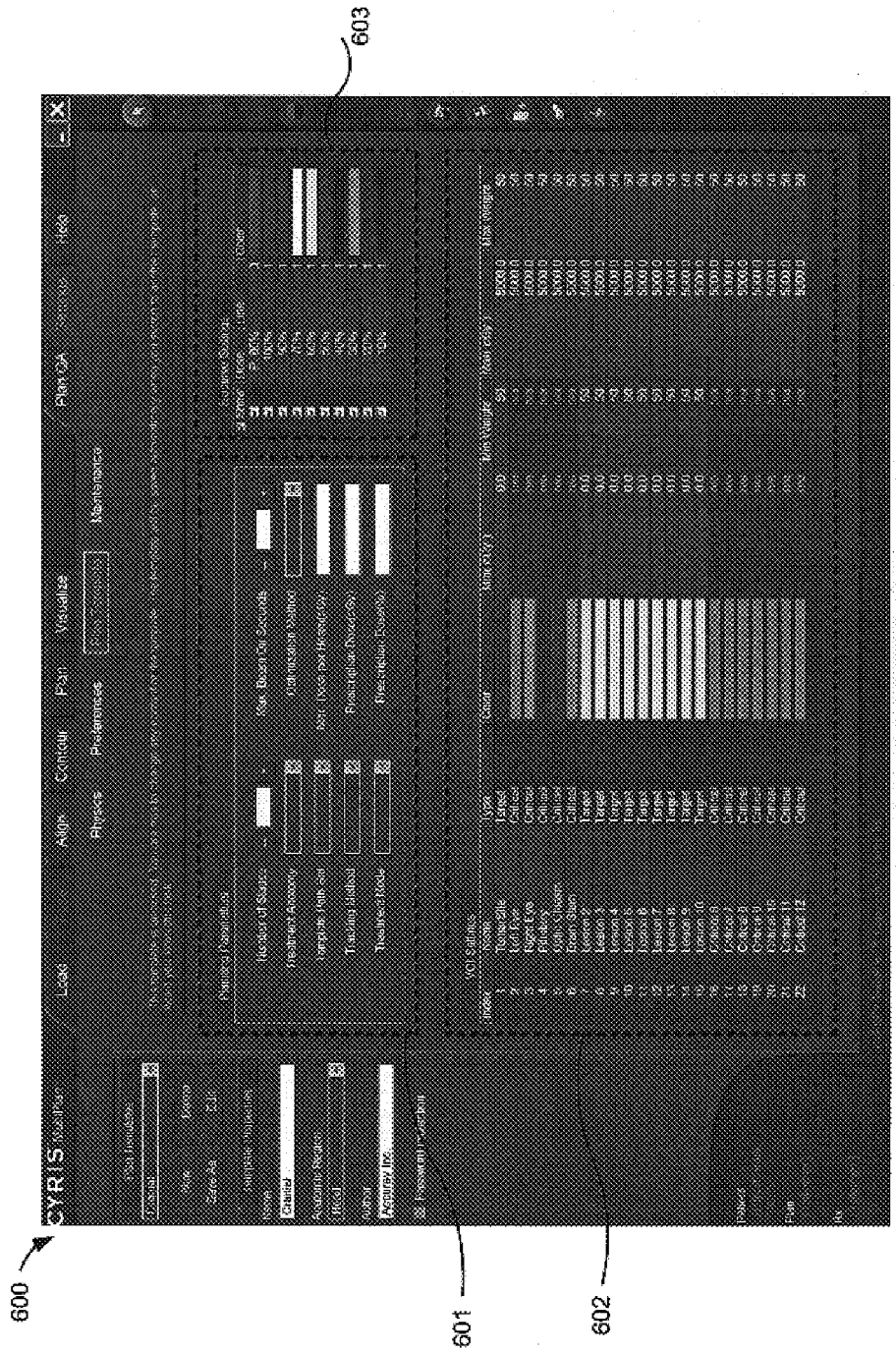
FIG. 11 illustrates an example of a user interface for a plan template that includes a set of treatment parameters.

By clicking on a template name (e.g., Cranial), a set of parameters for a treatment plan is loaded into the TPS. FIG. 11 illustrates an example of a user interface for a plan template 600 that includes a set of treatment parameters. In one embodiment, the plan template stores a set of parameters in the following areas: Plan Parameters 601, VOI Settings 602, and Isocurve Settings 603. Settings for Plan Parameters 601 include, for example, number of stages, treatment anatomy, treatment path set and tracking method. Settings for VOI Settings 602 include, for example, VOI name, VOI type, minimum/maximum dose constraint for the VOI (in cGy), weight for and width of line, in pixels, when displaying the VOI contours on a 2D image. Settings for Isocurve Settings 603 include, for example, level of the isocurve, color for displaying the isocurve on 2D images, and the width of the line, in pixels, when displaying the isocurve on 2D images.

After a plan template has been selected by a user, the treatment planning process may then enter into a workflow to create a treatment plan. In one embodiment, the workflow may include the tasks from Load to Visualize as described above. In an alternative embodiment, the workflow may begin with the Fuse task if the launch wizard is used. The workflow includes multiple planning tasks, with each task designed to address a particular aspect of treatment planning through a user interface.

Figure 12:
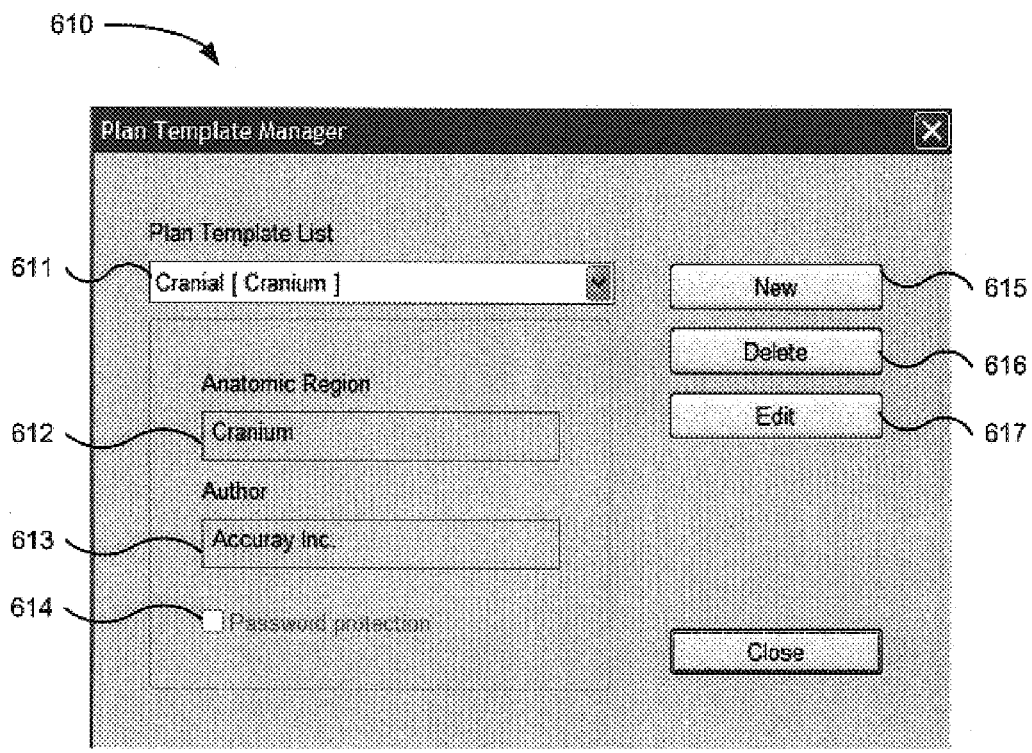
FIG. 12 illustrates an example of a template manager dialogue interface and the controls associated with the interface.

In one embodiment, the TPS may also include a template plan manager to allow the user to create or modify templates. The plan template manager may be a dialogue-based user interface. FIG. 12 illustrates an example of a template manager dialogue interface 610 and the controls associated with the interface. The Plan Template List control 611 may be a combo list that contains the names of all the plan templates available in the TPS. The type of each of the templates may also be shown as a postfix of the template name (e.g., Cranium). The Anatomic Region control 612 displays the anatomic region of the current selected plan template. The Author control 613 displays the name of the author of the current selected plan template. The template manager dialogue interface 610 may also include a Password Protection control 614 to indicate whether selected plan template is protected by a password.

Figure 13:
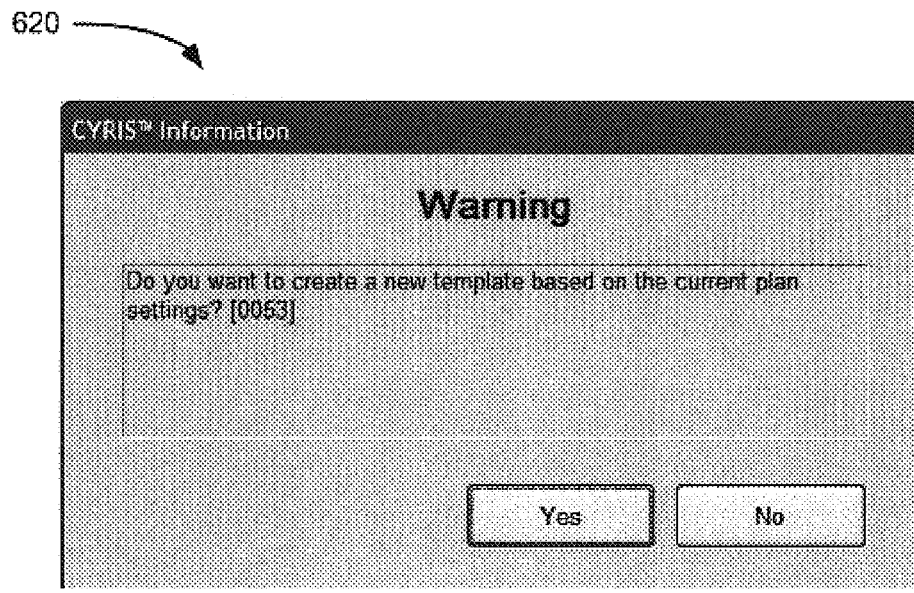
FIG. 13 illustrates an example of a dialogue box.
Figure 14:
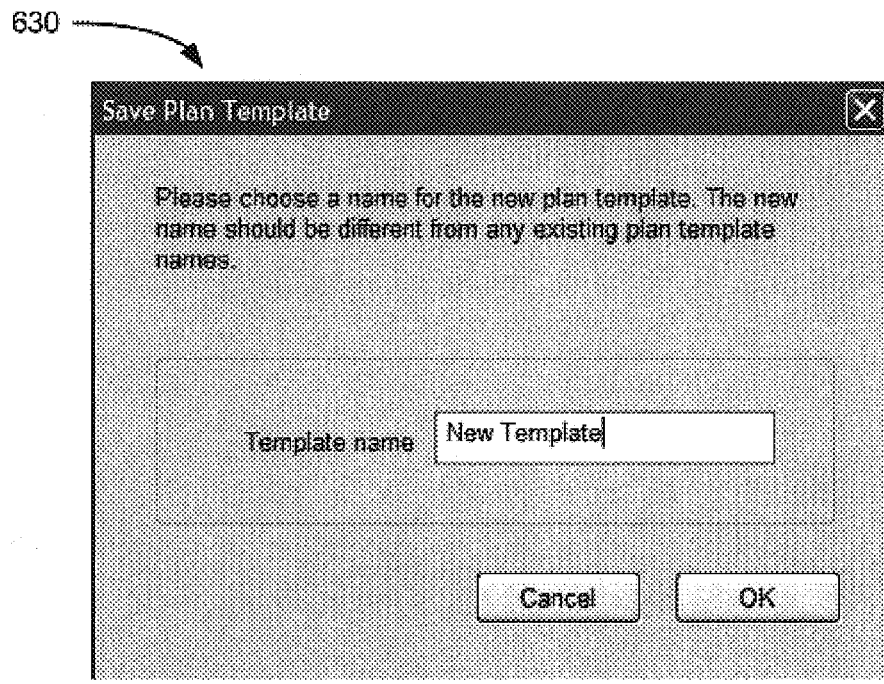
FIG. 14 illustrates another example of a dialogue box.
Figure 15:
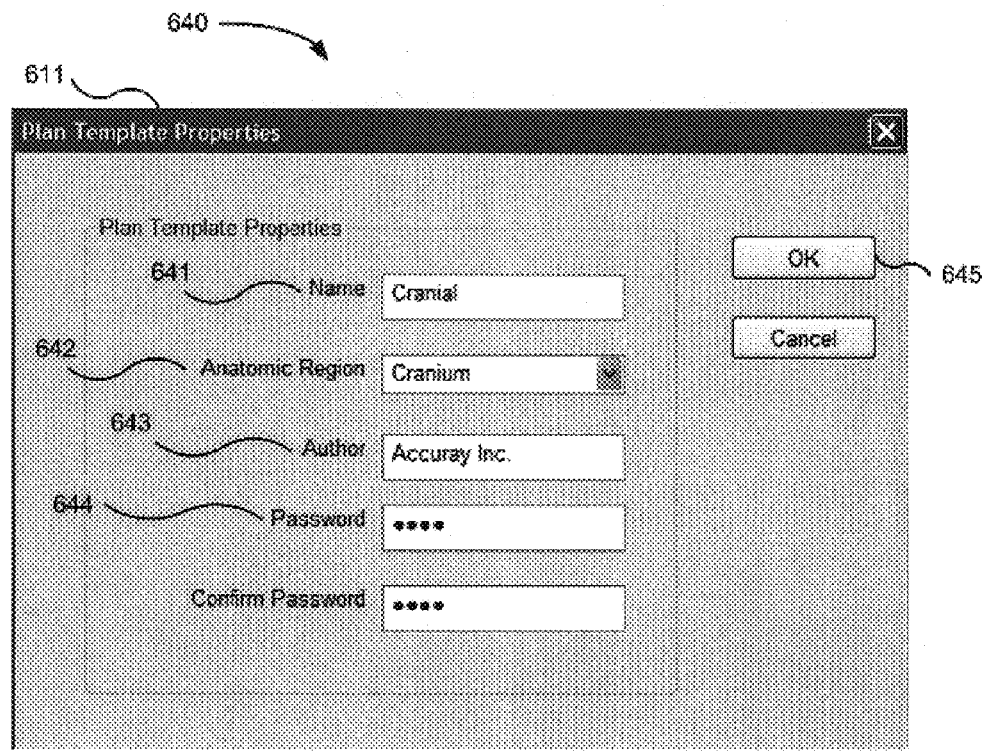
FIG. 15 illustrates another example of a dialogue box.

In another embodiment, the template plan manager allows the user to create a new template by clicking the "New" button 615 as shown in FIG. 12. Alternatively, "Delete" button 616 and "Edit" button 617 are also provided. In one embodiment, a dialog box 620 as shown in FIG. 13 may be displayed to the user, which asks the user whether the new template is based on the current plan settings such as the plan parameters, VOI template, and isocurve template (e.g., the plan settings of FIG. 11). The Save Plan Template dialogue box 630 shown in FIG. 14 is then displayed, which asks the user for a new template name. Next, a Plan Template Properties dialogue box 640 of FIG. 15 may be displayed to the user, which includes the following properties: Name 641, Anatomic Region 642, Author 643, and Password 644. If the user changes any of the fields and clicks the "OK" button 645, the changes are then saved to the newly created template. If the name the user inputs is identical to another existing template, the TPS may display another dialogue box to ask the user for permission to overwrite that template. In an alternative embodiment, another dialogue box (not shown) may be displayed when a password-protected plan template is deleted or edited. The delete or edit operation may be terminated unless the user types the correct password that has been saved with the plan template.

LOAD. The Load task may be the first step of the workflow in the absence of the launch wizard. In one embodiment, the LOAD task is divided into several steps using the launch wizard user interface as described above with respect to FIGS. 7-9. The LOAD task allows the user to load previously saved plans, start a new plan by loading DICOM formatted patient data, including volumes of interest pushed as DICOM RT structure sets, recover the last plan worked on, or delete a previously saved plan.

Figure 4:
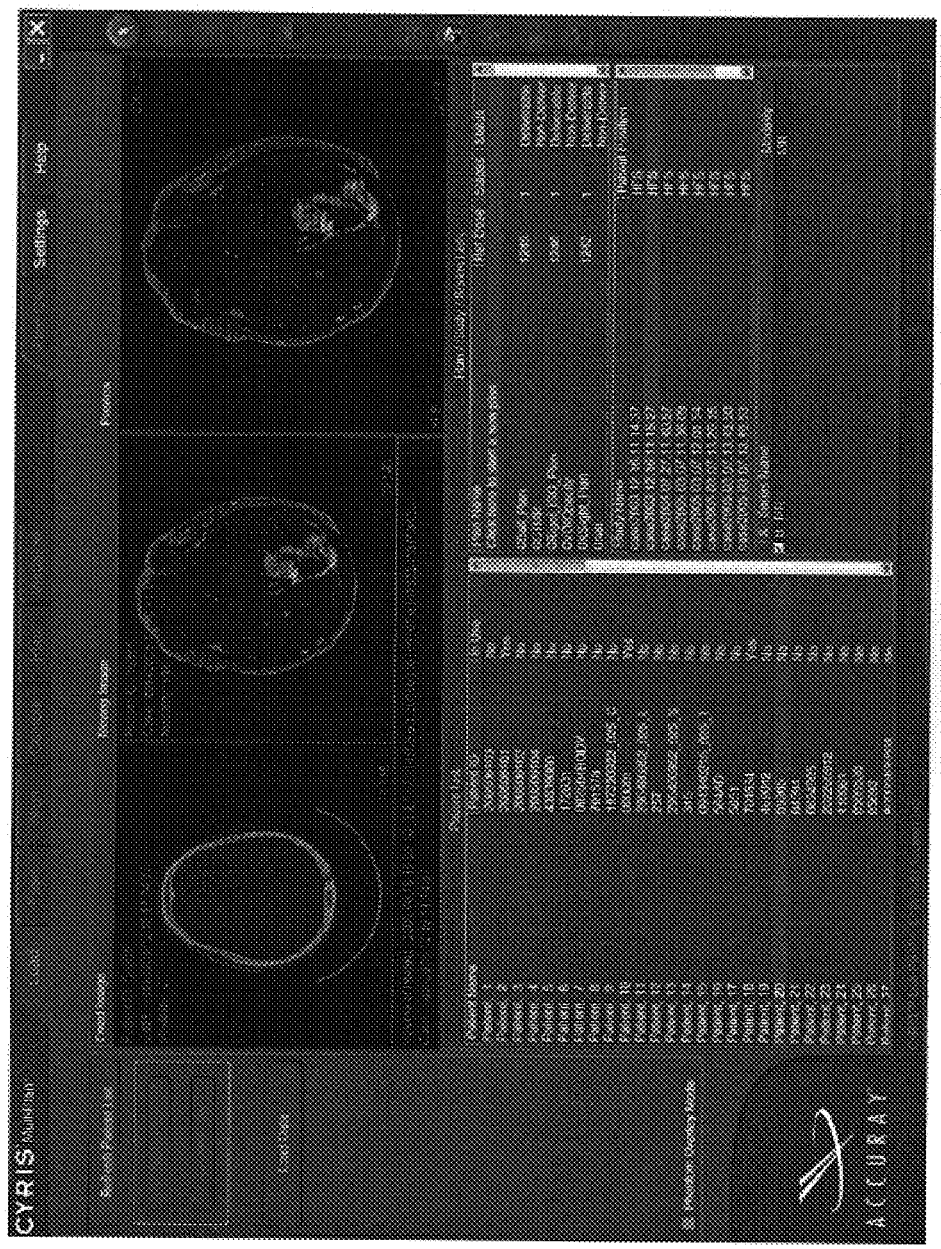
FIG. 4 illustrates one example of a user interface for a LOAD task.
Figure 5:
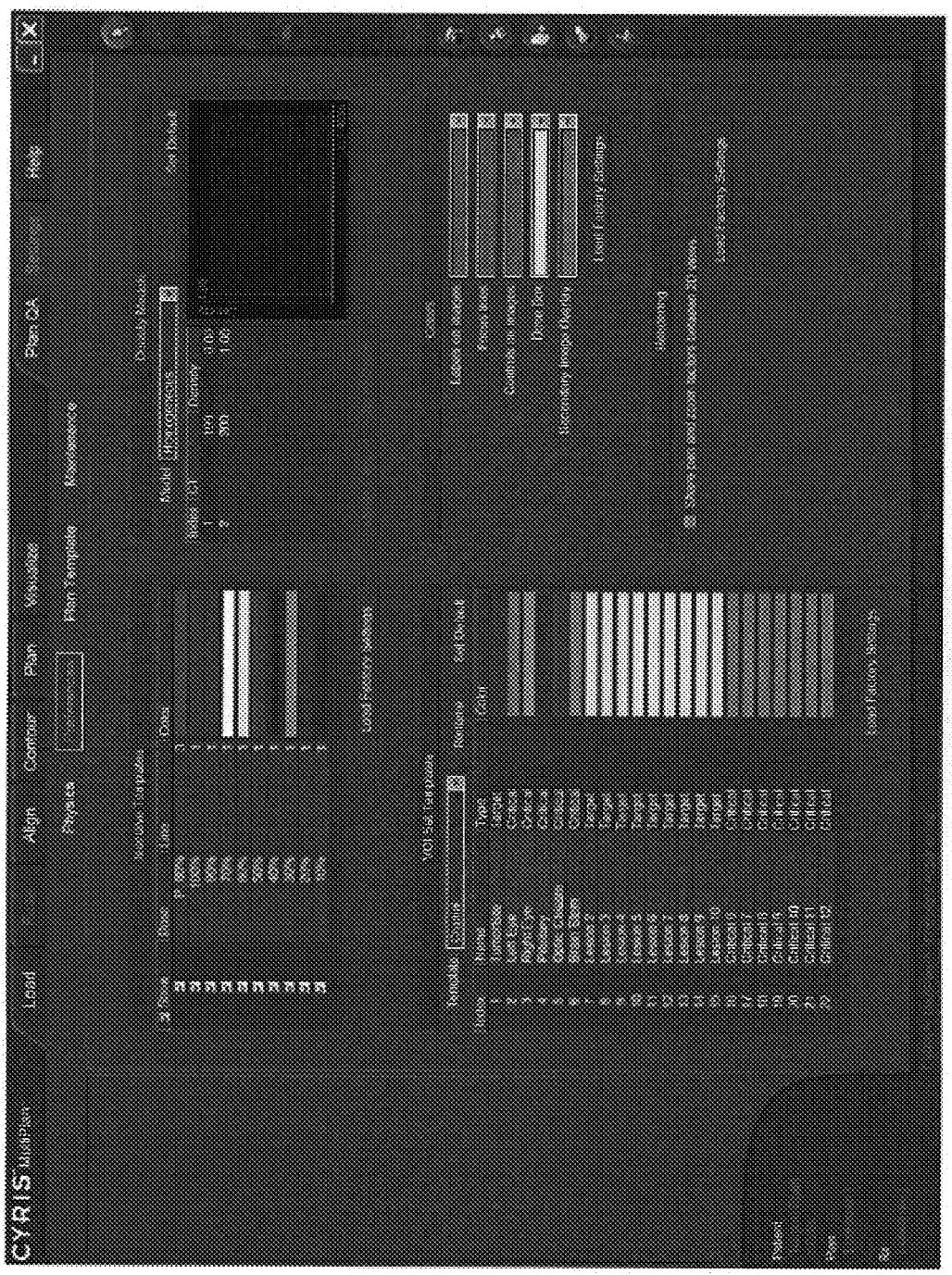
FIG. 5 illustrates a user interface for preference settings.

The user interface of FIG. 4, which shows the LOAD task display, includes a fixed image and a moving image. For example, the fixed image may be a CT image and the moving image may be a MR or PET image. The use of multiple image modalities is beneficial for treatment planning. A CT image is often selected because its data is used to track patient movement. MR or PET images may provide improved views of the pathological anatomy compared to CT images. The fixed and moving correspond to the selected patient. For example, once a particular patient is selected, a list of studies corresponding to that patient is displayed. Then for each study selected, a list of images is displayed. The fixed medical image, typically a CT image, may be selected by first the desired study from the study list and the desired CT image from the image list. As with the fixed image, the user selects the moving image by first selecting the patient, study, and list of images.

FUSE. With the fixed and moving images loaded by the TPS, the next step is to fuse the images together. In order for the user to contour structures such as the pathological and critical structures, the fixed and moving images are aligned together in a common space so that one image can be overlaid over the other image. In one embodiment, the CT fixed image and the MR moving image may be three-dimensional reconstructions when viewed on the display. The fusing of two image modalities first involves selecting multiple seed points that are approximately in similar places for both images, in order to get an idea of how the two images initially align. When the seed points have been selected in the fixed and moving images, the Register step in enabled in the TPS.

In one embodiment, he fixed and moving images are fused by employing a matrix algebra solution that performs an initial alignment of the two images based on the selected seed points from each image. The user may then have the TPS perform a refinement process after the initial Register step. By selecting the "Start" button, the TPS executes an algorithm to improve the alignment of the two images. During the refinement process, the user can manipulate the split views to evaluate the quality of the fusion. Two-dimensional images are used merely to show the result of the fusion process, but the actual optimization is performed on the four three-dimensional volumes. It should also be noted that fusion of the fixed and moving images may be performed without the use of seed points. The images may be taken as they are and fused either manually or with the algorithm of the TPS.

Figure 16:
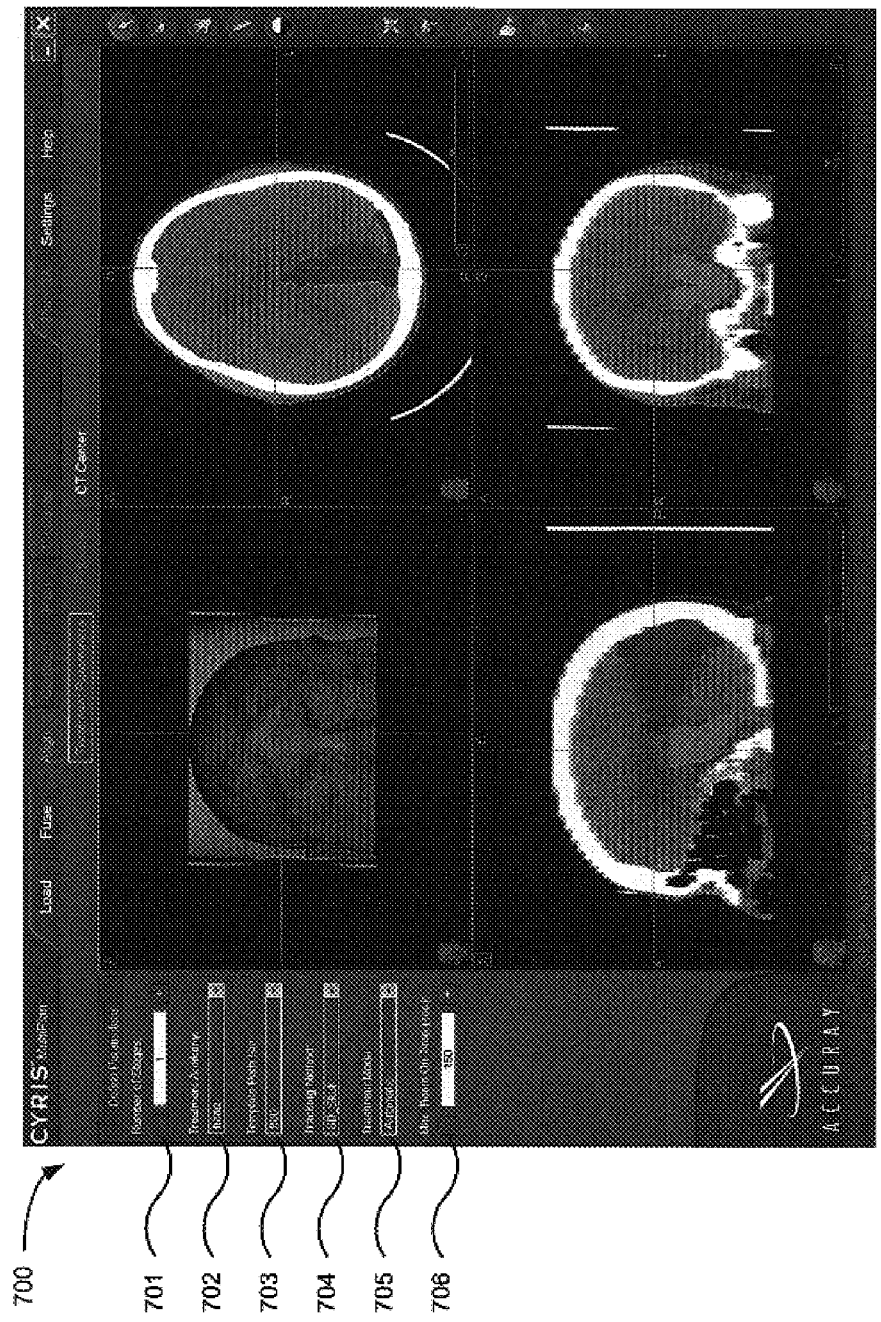
FIG. 16 illustrates a user interface for setting treatment parameters.

ALIGN. After the fusion of fixed and moving images is completed, the next step is to establish parameters that describe the treatment to be performed on the patient. FIG. 16 illustrates a user interface 700 for setting treatment parameters. In one embodiment, the treatment parameters shown on FIG. 16 may be automatically inputted according to the settings of the selected template (determined during the launch wizard process described above). Parameters such as number of stages 701, treatment anatomy 702, template path set 703, tracking method 704, treatment mode 705, and maximum beam on time 706 may be pre-set so that the user does not have to input these parameters manually, as would be required in the workflow of conventional treatment planning process. Number of stages 701 refers to the total number of stages in the treatment. In radiosurgery, the overall treatment is typically divided into a set of steps instead of giving the patient the entire radiation dose in one session. This is referred to as "fractionation." For example, the total treatment dose may be divided over five treatment sessions, because there may be critical structures adjacent to the pathological anatomy that may not be able to tolerate the total radiation dose if performed in one session. By dividing the treatment into multiple sessions, the critical regions that may be exposed to radiation are given time to recover and heal to a certain extent. Depending on the dose delivered to the patient, it may not be necessary to dive the treatment into multiple sessions. Here, the user is allowed to define the number of treatment stages.

Treatment Anatomy 702 and Path Set 703 are additional parameters that may be automatically set according to a selected template. Treatment Anatomy 702 informs the treatment planning and delivery system of the general anatomical area to be treated. In this embodiment, the treatment anatomy is "head." Path Set 703 defines the set of positions for the robotic arm from which to fire the radiation beams. The TPS may provide a number of templates with different sets of beam positions, depending on the treatment anatomy selected. Tracking Method 704 and Treatment Mode 705 are other parameters that may be automatically set according to a selected template. Tracking method 704 (e.g., 6D_Skull) defines how the imaging system automatically takes x-ray shots of the patient while the patient is being treated, and the treatment delivery system uses the data from the x-ray images to determine the exact position of the patient during treatment, allowing the robot to make adjustments in case the patient moves during treatment. Treatment Mode 705 (e.g., automatic or manual) allows the treatment delivery system to control the timing for the diagnostic images and the firing of individual beams. Alternatively, the user may instruct the system to take diagnostic images and fire individual beams.

During treatment delivery, the machine center should be aligned with the CT image so that the imaging system may function correctly. This is accomplished by defining the CT image center and the position of the patient during treatment through a user interface. In one embodiment, the position of the patient on the treatment couch is used to define the CT center. By aligning the machine center with the CT center, the treatment delivery and imaging systems can produce the desired images (e.g., x-ray images) of the patient during treatment when the patient is properly aligned with the treatment delivery system.

Figure 17:
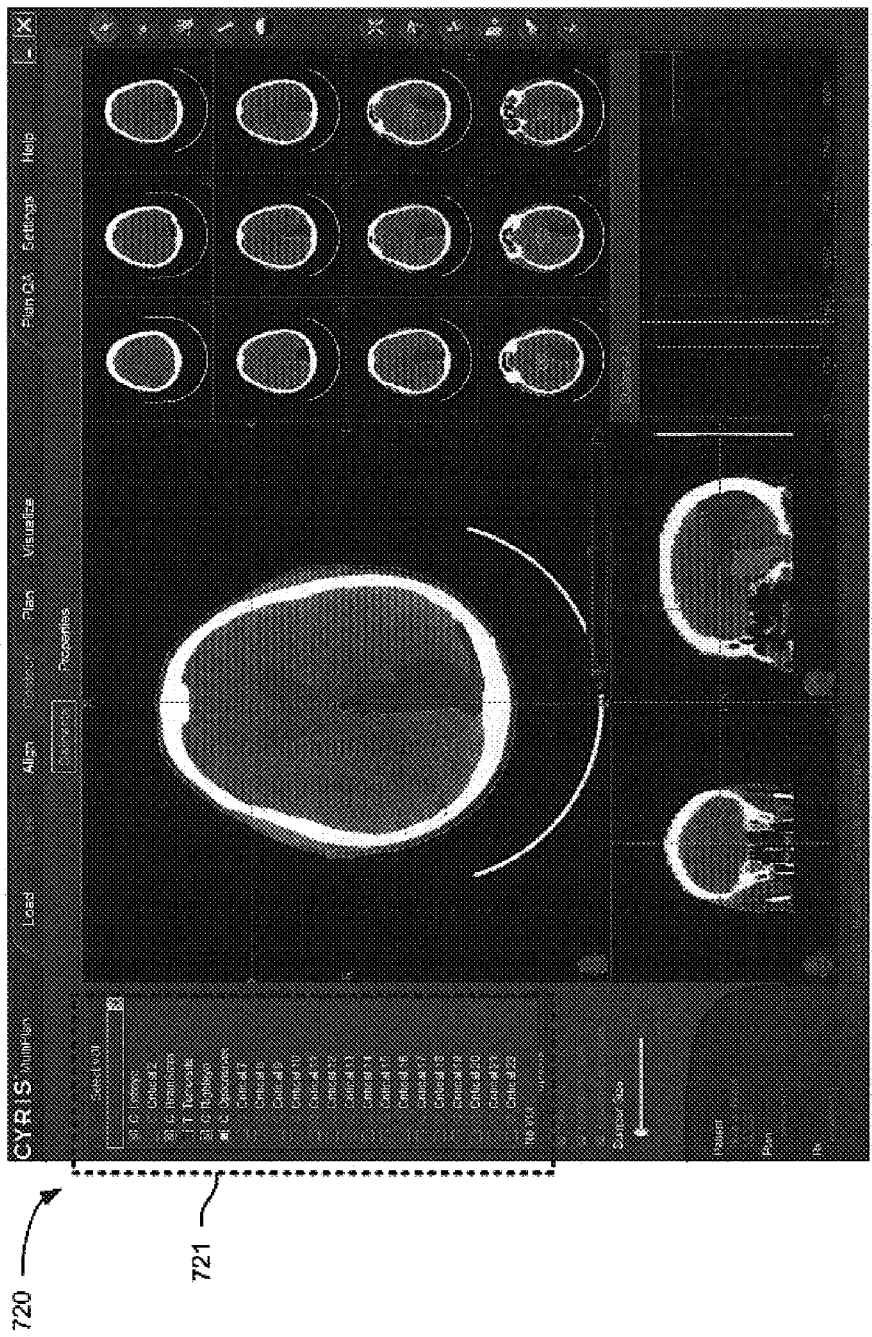
FIG. 17 illustrates a user interface for the Delineate step.

CONTOUR. The next task of treatment planning is creating and modifying anatomical volumes of interest. This task includes two steps: Delineate and Properties. The Delineate step includes drawing tools for the user to draw and edit volumes of interest. The Properties step allows the user to change specific tags and display setting associated with each volume of interest. If a selected plan template is loaded, the user interface 720 for the Delineate step, as shown in FIG. 17, already includes the various VOIs 721, such as left eye, tumor site, brain stem, right eye, and optic nerve. Without the use of the plan template, the user would be required to identify each VOI manually.

The volume of interest (VOI) is a user-defined region overlain on the medical images that typically represents a distinct anatomical feature such as the pathological anatomy targeted for treatment or critical structures to avoid radiation. For example, using the moving image such as a two-dimensional MR image, the user identifies and designates the pathological anatomy as the target region by drawing or contouring a line around the pathological anatomy. This process may be repeated for additional two-dimensional slices of MR images. In one embodiment, the contour from one slice is reproduced on the next slice so that a bumper tool may be used modify the contour without having to re-draw a new line. This process may be performed separately for the pathological anatomy and any critical structures.

After contouring several slices, the TPS may perform an interpolation of all the two-dimensional slices for a particular image modality so that the operator does not have to contour each and every two-dimensional slice. For example, the TPS provides automatic interpolation to reduce the time required to generate a contour set. When a user draws a contour on one slice and a second contour on a second slice for the pathological anatomy, the contours for slices between the first slice and the second slice are automatically determined using linear interpolation. Interpolating all the slices for a particular type of image may not be appropriate for certain types of anatomical regions. For example, anatomical structures may change significantly from slice to slice may be too dramatic for the TPS to interpolate properly. In contrast, an anatomical structure such as the spinal chord that has fairly consistent dimensions from slice to slice may be interpolated accurately by the TPS, thereby reducing the number of slices that would require contouring.

Figure 18:
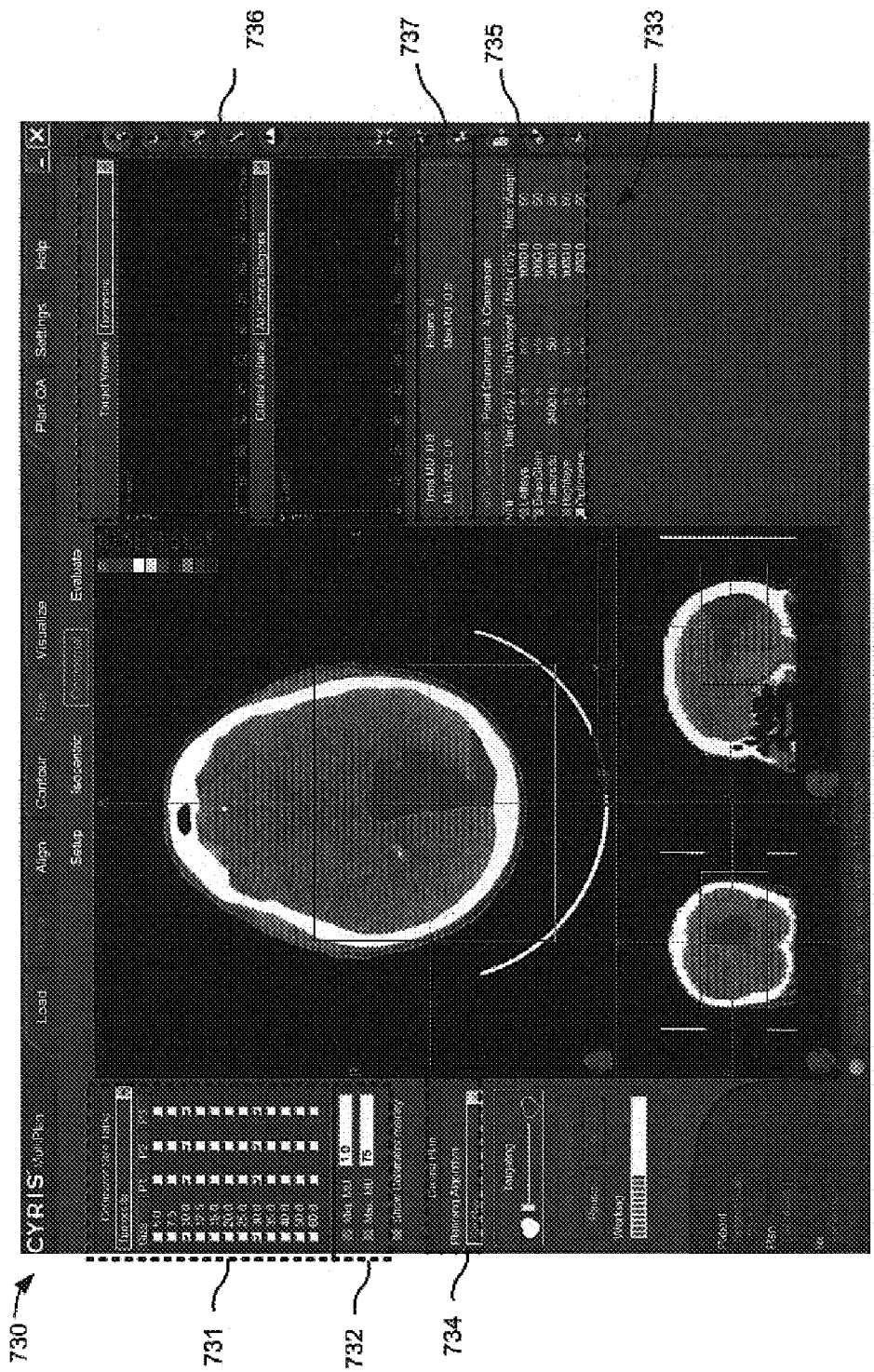
FIG. 18 illustrates a user interface for conformal planning.

PLAN. The Plan task contains the functionality for creating, refining, and reviewing treatment plans. The TPS supports isocentric, conformal, and mixed isocentric/conformal planning. In conformal planning, the TPS uses an iterative optimizer to produce conformal plans giving a balance of homogeneity and conformality. Conformal planning takes advantage of the CyberKnife® system because the robot can move around freely in at least six dimensions, allowing the radiation beams to point anywhere in space, unlike isocenter-based systems such as the GammaKnife, which involves treatment plans that stack multiple isocenters within a treatment area. An isocenters is a common point in which a set of beams all converge. In order to start a conformal plan, at least one region designated as a target is defined. The user interface 730 for conformal planning is illustrated in FIG. 18.

In conformal planning, some beams may or may not intersect or converge at a common point. The radiation beams need only intersect with the target volume and do not necessarily converge on a single point, or isocenter, within the target. The initial beam weights may be a default beam weight determined by the operator or the TPS. The initial beam weights may also be influenced by the prescribed radiation dose to be delivered to a target region. For example, if a total prescribed dose of 3500 cGy is set for a target region, the TPS would automatically determine the beam weights for each beam to balance conformality and homogeneity to achieve that prescribed dose as closely as possible.

The Plan task is another area of the treatment planning workflow in which the use of templates provides an advantage to the user. As with other tasks of the treatment plan workflow, various settings for the Plan task may be automatically inputted by the template settings. Typically, the first step of the Plan task is defining certain parameters what will be used in the treatment planning process. One parameter for conformal planning is collimator size 731, which is provided by a collimator size table. Collimator size refers to the thickness of the radiation beam originating from the linear accelerator. For a selected target (e.g., pathological anatomy), a collimator size (e.g., 15.0, 30.0) and one or more paths (e.g., P1, P2, P3) available for that collimator size may be preset according to the settings of a template. Another parameter is minimum/maximum monitor units (MU) 732 allowed for the beams aimed at the selected target. The plan template settings may also define a minimum dose constraint for the target region and a maximum dose constraint for a critical region (shown in panel 733 of FIG. 18). For example, a minimum dose constraint of 2400 cGy is set for the tumor site and a maximum dose constraint of 1200 cGy is set for the brain stem critical region as shown in FIG. 18.

The TPS provides two algorithms for optimizing the dose distribution based on the user defined minimum/maximum dose constraints. The first option is an iterative algorithm that optimizes deviations above the maximum dose constraint and below the minimum dose constraint. The iterative planning algorithm first generates a set of beams and performs an initial dose distribution calculation, and subsequently attempts to improve the initial dose distribution calculation by altering one or more beams. The second option is a simplex algorithm, which involves minimizing the number of MUs subject to the minimum/maximum dose constraints. The use of either an iterative or a simplex algorithm 734 is another setting that may be preset by a template. In one embodiment, a combination of both algorithms may be used. For example, the plan optimization may begin with the simplex algorithm to determine the minimal MU required, followed by the iterative algorithm.

In another embodiment, the plan template may also provide setting for the addition for deletion of constraint points 735 to improve the shape of the dose isocontour. Dose Constraint Panel 733 is provided near the right side of the display with button near the bottom which also allows the user to manually Add, Delete, or Delete All of the point constraints. The constraints are listed above these buttons. For each point constraint is added, the template may define whether that constraint point is a minimum or maximum constraint, the limit value, and the weight. The point constraint may appear as a small-dot on the planar view. Dose Constraint Panel 733 also includes settings 737 for Total MU, number of beams, Minimum MU, and Maximum MU. These settings may also be pre-set according to a selected template.

Near the right side of the conformal user interface 730 of FIG. 18 are DVHs 736 for the target and critical regions. For example, the top DVH corresponds to the target region and the bottom DVH corresponds to the right eye critical region. With each optimization procedure (e.g., using the iterative algorithm), the resultant DVHs may be displayed.

In one embodiment, the treatment planning process may involve aspects of both forward and inverse planning techniques, thereby combining the strengths of forward and inverse planning techniques. For example, the operator can utilize isocentric beam geometries or a mixture of non-isocentric and isocentric beam geometries as part of forward planning and subsequently modify the topology of isodose contours directly during inverse planning. The operator can control each beam for use in the treatment plan in terms of radiation emission point, a distance to the target region, an orientation, and a radiation dose weight. Alternatively, the characteristics of each beam may be pre-set according to the settings of a selected template. The TPS can allow the operator to specify a set of beams (and associated paths, emission points, and dose weights) to be used as part of a forward planning process, and another set of beams to be used as part of inverse planning. The set of beams reserved for inverse planning may be optimized by utilizing one or more envelope of constraint points generated automatically by the treatment planning software.

Figure 19:
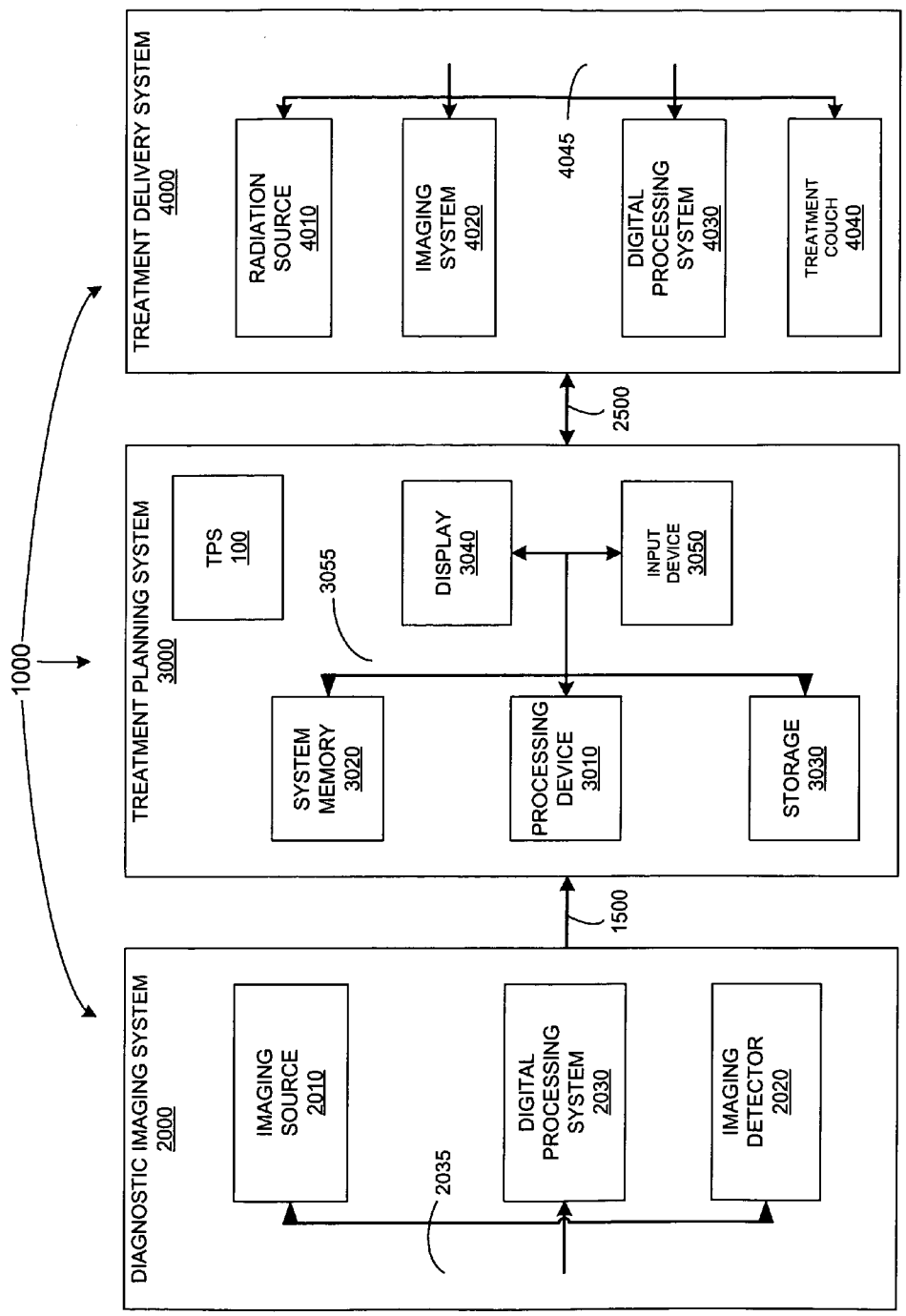
FIG. 19 illustrates one embodiment of systems that may be used to perform radiation treatment in which features of the present invention may be implemented.

FIG. 19 illustrates one embodiment of systems that may be used to perform radiation treatment in which features of the present invention may be implemented. As described below and illustrated in FIG. 19, system 1000 may include a diagnostic imaging system 2000, a treatment planning system 3000, and a treatment delivery system 4000.

Diagnostic imaging system 2000 may be any system capable of producing medical diagnostic images of a volume of interest (VOI) in a patient that may be used for subsequent medical diagnosis, treatment planning and/or treatment delivery. For example, diagnostic imaging system 2000 may be a computed tomography (CT) system, a magnetic resonance imaging (MRI) system, a positron emission tomography (PET) system, an ultrasound system or the like. For ease of discussion, diagnostic imaging system 2000 may be discussed below at times in relation to a CT x-ray imaging modality. However, other imaging modalities such as those above may also be used.

Diagnostic imaging system 2000 includes an imaging source 2010 to generate an imaging beam (e.g., x-rays, ultrasonic waves, radio frequency waves, etc.) and an imaging detector 2020 to detect and receive the beam generated by imaging source 2010, or a secondary beam or emission stimulated by the beam from the imaging source (e.g., in an MRI or PET scan). In one embodiment, diagnostic imaging system 2000 may include two or more diagnostic X-ray sources and two or more corresponding imaging detectors. For example, two x-ray sources may be disposed around a patient to be imaged, fixed at an angular separation from each other (e.g., 90 degrees, 45 degrees, etc.) and aimed through the patient toward (an) imaging detector(s) which may be diametrically opposed to the x-ray sources. A single large imaging detector, or multiple imaging detectors, may also be used that would be illuminated by each x-ray imaging source. Alternatively, other numbers and configurations of imaging sources and imaging detectors may be used.

The imaging source 2010 and the imaging detector 2020 are coupled to a digital processing system 2030 to control the imaging operation and process image data. Diagnostic imaging system 2000 includes a bus or other means 2035 for transferring data and commands among digital processing system 2030, imaging source 2010 and imaging detector 2020. Digital processing system 2030 may include one or more general-purpose processors (e.g., a microprocessor), special purpose processor such as a digital signal processor (DSP) or other type of device such as a controller or field programmable gate array (FPGA). Digital processing system 2030 may also include other components (not shown) such as memory, storage devices, network adapters and the like. Digital processing system 2030 may be configured to generate digital diagnostic images in a standard format, such as the DICOM (Digital Imaging and Communications in Medicine) format, for example. In other embodiments, digital processing system 2030 may generate other standard or non-standard digital image formats. Digital processing system 2030 may transmit diagnostic image files (e.g., the aforementioned DICOM formatted files) to treatment planning system 3000 over a data link 1500, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 3000 includes a processing device 3010 to receive and process image data. Processing device 3010 may represent one or more general-purpose processors (e.g., a microprocessor), special purpose processor such as a digital signal processor (DSP) or other type of device such as a controller or field programmable gate array (FPGA). Processing device 3010 may be configured to execute instructions for performing the TPS 100 operations discussed herein, for example, guiding the user through the launch wizard and/or allowing the user to select a plan template.

Treatment planning system 3000 may also include system memory 3020 that may include a random access memory (RAM), or other dynamic storage devices, coupled to processing device 3010 by bus 3055, for storing information and instructions to be executed by processing device 3010. System memory 3020 also may be used for storing temporary variables or other intermediate information during execution of instructions by processing device 3010. System memory 3020 may also include a read only memory (ROM) and/or other static storage device coupled to bus 3055 for storing static information and instructions for processing device 3010.

Treatment planning system 3000 may also include storage device 3030, representing one or more storage devices (e.g., a magnetic disk drive or optical disk drive) coupled to bus 3055 for storing information and instructions. Storage device 3030 may be used for storing instructions for performing the treatment planning steps discussed herein, such as the dilution and erosion algorithms.

Processing device 3010 may also be coupled to a display device 3040, such as a cathode ray tube (CRT) or liquid crystal display (LCD), for displaying information (e.g., a two-dimensional or three-dimensional representation of the VOI) to the user. An input device 3050, such as a keyboard, may be coupled to processing device 3010 for communicating information and/or command selections to processing device 3010. One or more other user input devices (e.g., a mouse, a trackball or cursor direction keys) may also be used to communicate directional information, to select commands for processing device 3010 and to control cursor movements on display 3040.

It will be appreciated that treatment planning system 3000 represents only one example of a treatment planning system, which may have many different configurations and architectures, which may include more components or fewer components than treatment planning system 3000 and which may be employed with the present invention. For example, some systems often have multiple buses, such as a peripheral bus, a dedicated cache bus, etc. The treatment planning system 3000 may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view dose distributions on any one of various imaging modalities (e.g., MRI, CT, PET, etc.). Treatment planning systems are known in the art; accordingly, a more detailed discussion is not provided.

Treatment planning system 3000 may share its database (e.g., data stored in storage device 3030) with a treatment delivery system, such as treatment delivery system 4000, so that it may not be necessary to export from the treatment planning system prior to treatment delivery. Treatment planning system 3000 may be linked to treatment delivery system 4000 via a data link 2500, which may be a direct link, a LAN link or a WAN link as discussed above with respect to data link 1500. It should be noted that when data links 1500 and 2500 are implemented as LAN or WAN connections, any of diagnostic imaging system 2000, treatment planning system 3000 and/or treatment delivery system 4000 may be in decentralized locations such that the systems may be physically remote from each other. Alternatively, any of diagnostic imaging system 2000, treatment planning system 3000 and/or treatment delivery system 4000 may be integrated with each other in one or more systems.

Treatment delivery system 4000 includes a therapeutic and/or surgical radiation source 4010 to administer a prescribed radiation dose to a target volume in conformance with a treatment plan. Treatment delivery system 4000 may also include an imaging system 4020 to capture intra-treatment images of a patient volume (including the target volume) for registration or correlation with the diagnostic images described above in order to position the patient with respect to the radiation source. Treatment delivery system 4000 may also include a digital processing system 4030 to control radiation source 4010, imaging system 4020, and a patient support device such as a treatment couch 4040. Digital processing system 4030 may include one or more general-purpose processors (e.g., a microprocessor), special purpose processor such as a digital signal processor (DSP) or other type of device such as a controller or field programmable gate array (FPGA). Digital processing system 4030 may also include other components (not shown) such as memory, storage devices, network adapters and the like. Digital processing system 4030 may be coupled to radiation source 4010, imaging system 4020 and treatment couch 4040 by a bus 4045 or other type of control and communication interface.

Figure 20:
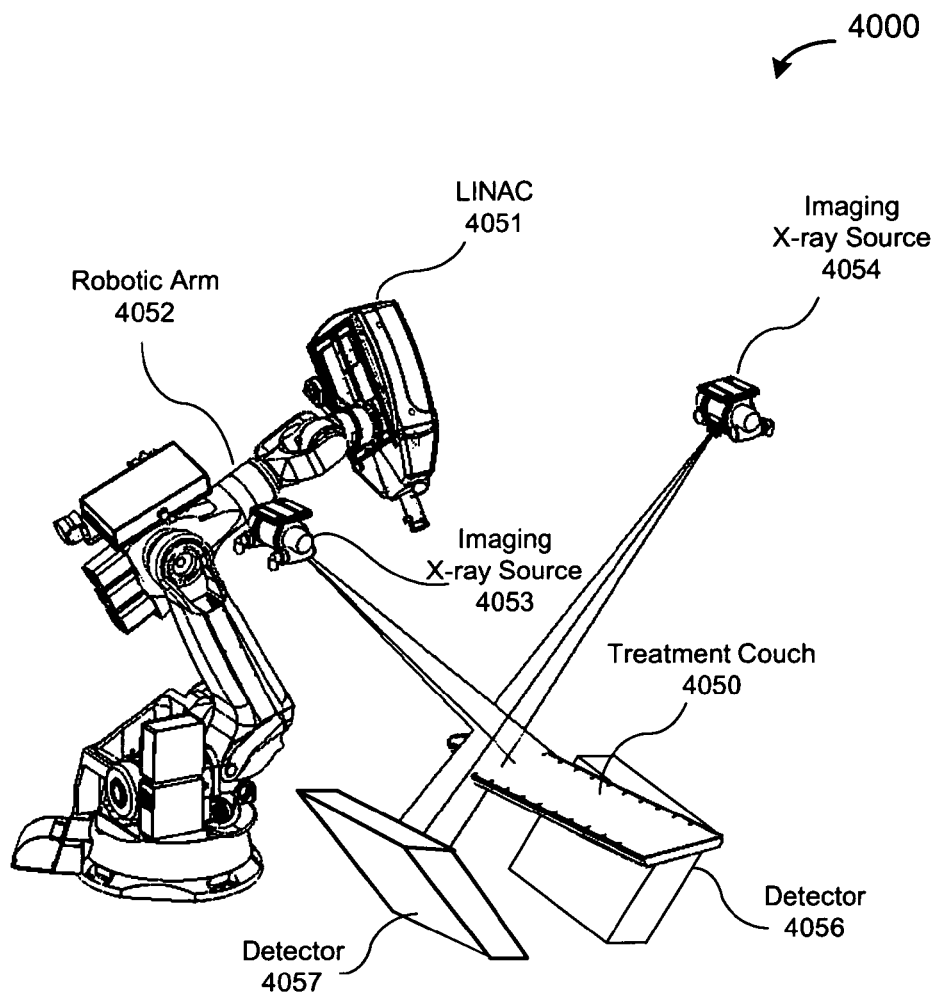
FIG. 20 illustrates one embodiment of a treatment delivery system.

In one embodiment, as illustrated in FIG. 20, treatment delivery system 4000 may be an image-guided, robotic-based radiation treatment system (e.g., for performing radiosurgery) such as the CyberKnife® system developed by Accuray Incorporated of California. In FIG. 21, radiation source 4010 may be represented by a linear accelerator (LINAC) 4051 mounted on the end of a robotic arm 4052 having multiple (e.g., 5 or more) degrees of freedom in order to position the LINAC 4051 to irradiate a pathological anatomy (target region or volume) with beams delivered from many angles in an operating volume (e.g., a sphere) around the patient. Treatment may involve beam paths with a single isocenter (point of convergence), multiple isocenters, or with a non-isocentric approach (i.e., the beams need only intersect with the pathological target volume and do not necessarily converge on a single point, or isocenter, within the target). Treatment can be delivered in either a single session (mono-fraction) or in a small number of sessions as determined during treatment planning. With treatment delivery system 4000, in one embodiment, radiation beams may be delivered according to the treatment plan without fixing the patient to a rigid, external frame to register the intra-operative position of the target volume with the position of the target volume during the pre-operative treatment planning phase.

In FIG. 20, imaging system 4020 may be represented by X-ray sources 4053 and 4054 and X-ray image detectors (imagers) 4056 and 4057. In one embodiment, for example, two x-ray sources 4053 and 4054 may be nominally aligned to project imaging x-ray beams through a patient from two different angular positions (e.g., separated by 90 degrees, 45 degrees, etc.) and aimed through the patient on treatment couch 4050 toward respective detectors 4056 and 4057. In another embodiment, a single large imager can be used that would be illuminated by each x-ray imaging source. Alternatively, other numbers and configurations of imaging sources and imagers may be used.

Digital processing system 4030 may implement algorithms to register images obtained from imaging system 4020 with pre-operative treatment planning images in order to align the patient on the treatment couch 4050 within the treatment delivery system 4000, and to precisely position the radiation source with respect to the target volume.

The treatment couch 4050 may be coupled to another robotic arm (not illustrated) having multiple (e.g., 5 or more) degrees of freedom. The couch arm may have five rotational degrees of freedom and one substantially vertical, linear degree of freedom. Alternatively, the couch arm may have six rotational degrees of freedom and one substantially vertical, linear degree of freedom or at least four rotational degrees of freedom. The couch arm may be vertically mounted to a column or wall, or horizontally mounted to pedestal, floor, or ceiling. Alternatively, the treatment couch 4050 may be a component of another mechanical mechanism, such as the Axum® treatment couch developed by Accuray Incorporated of California, or be another type of conventional treatment table known to those of ordinary skill in the art.

Alternatively, treatment delivery system 4000 may be another type of treatment delivery system, for example, a gantry based (isocentric) intensity modulated radiotherapy (IMRT) system. In a gantry based system, a radiation source (e.g., a LINAC) is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator that allows portions of the beam to be blocked, so that the remaining beam incident on the patient has a pre-defined shape. The resulting system generates arbitrarily shaped radiation beams that intersect each other at the isocenter to deliver a dose distribution to the target. In IMRT planning, the optimization algorithm selects subsets of the main beam and determines the amount of time that the patient should be exposed to each subset, so that the prescribed dose constraints are best met.

In other embodiments, yet another type of treatment delivery system 4000 may be used, for example, a stereotactic frame system such as the GammaKnife®, available from Elekta of Sweden. With such a system, the optimization algorithm (also referred to as a sphere packing algorithm) of the treatment plan determines the selection and dose weighting assigned to a group of beams forming isocenters in order to best meet provided dose constraints.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the application of radiation beam(s).

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method of developing a treatment plan for radiation therapy, comprising:
   providing an interface to a user to perform a plurality of treatment planning operations prior to plan optimization, the treatment planning operations including at least one of selecting a treatment planning parameter or inputting data corresponding to the treatment planning parameter;
   providing to the user one or more templates containing one or more pre-defined treatment planning parameters to enable the user to skip performing one or more of the plurality of operations, wherein the one or more pre-defined treatment planning parameters of said one or more templates are accepted or modified based on user input; and
   generating a treatment plan in response to receiving the user input.

2. The method of claim 1, wherein the one or more pre-defined treatment planning parameters relate to an anatomical region of interest.

3. The method of claim 1, wherein the one or more templates further contains one or more pre-defined treatment planning settings.

4. The method of claim 3, wherein the one or more pre-defined treatment planning settings are based on one or more past treatments.

5. The method of claim 3, wherein the one or more pre-defined treatment planning settings are pre-defined by a user.

6. The method of claim 3, wherein the one or more pre-defined treatment planning settings are pre-defined by a manufacturer of a treatment planning software that performs the above recited steps.

7. The method of claim 3, wherein the one or more pre-defined treatment planning parameters relate to an anatomical region of interest.

8. The method of claim 7, wherein the one or more pre-defined treatment planning settings are pre-defined by a learning process based on a previous treatment plan for the anatomical region of interest.

9. The method of claim 3, wherein the one or more pre-defined treatment planning settings comprises a node subset.

10. The method of claim 3, wherein the one or more pre-defined treatment planning settings comprises at least one of a number of stages, a treatment path set or a tracking method.

11. The method of claim 3, wherein the one or more pre-defined treatment planning settings comprises at least one of a volume of interest (VOI) name, a VOI type, a minimum dose constraint for a VOI, a maximum dose constraint for a VOI.

12. The method of claim 3, wherein the one or more pre-defined treatment planning settings comprises at least one of a level of an isocurve, color for displaying the isocurve on a two dimensional image, and a width of a line in pixels when displaying the isocurve on the two dimensional image.

13. The method of claim 1, further comprising presenting a plurality of steps to the user, each of the plurality of steps having corresponding information and data entry.

14. The method of claim 13, wherein a first step of the plurality of steps comprises selecting a patient.

15. The method of claim 14, wherein a second step of the plurality of steps comprises selecting a primary exam.

16. The method of claim 15, wherein selecting a primary exam comprises selecting an image.

17. The method of claim 15, wherein a second step of the plurality of steps comprises selecting an additional exam.

18. The method of claim 15, wherein selecting a primary exam comprises selecting an image and wherein selecting an additional exam comprises selecting an additional image.

19. The method of claim 13, wherein a step of the plurality of steps comprises selecting a template of the one or more templates.

20. The method of claim 19, further comprising:
    receiving as input a user selected template; and
    loading a set of treatment planning parameters based on the user selected template.

21. The method of claim 20, wherein the one or more templates contain one or more pre-defined treatment planning settings.

22. The method of claim 13, wherein the plurality of steps correspond to a load task.

* * * * *